US010392369B2

(12) United States Patent
Riether et al.

(10) Patent No.: US 10,392,369 B2
(45) Date of Patent: Aug. 27, 2019

(54) N-[(PYRIMIDINYLOXY)PROPANYL]BENZAMIDES

(71) Applicant: Boehringer Ingelheim International GmbH, Ingelheim am Rhein (DE)

(72) Inventors: Doris Riether, Biberach an der Riss (DE); Marco Ferrara, San Donato Milanese (IT); Niklas Heine, Biberach an der Riss (DE); Uta Lessel, Maselheim (DE); Janet Rachel Nicholson, Oberhoefen (DE); Anton Pekcec, Munich (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/090,325

(22) PCT Filed: Apr. 17, 2017

(86) PCT No.: PCT/EP2017/058312
§ 371 (c)(1),
(2) Date: Oct. 1, 2018

(87) PCT Pub. No.: WO2017/178338
PCT Pub. Date: Oct. 19, 2017

(65) Prior Publication Data

US 2019/0112295 A1 Apr. 18, 2019

(30) Foreign Application Priority Data

Apr. 15, 2016 (EP) .................................... 16165520

(51) Int. Cl.

| | |
|---|---|
| *C07D 403/12* | (2006.01) |
| *C07D 413/12* | (2006.01) |
| *A61K 31/506* | (2006.01) |
| *A61P 25/00* | (2006.01) |

(52) U.S. Cl.
CPC ......... *C07D 403/12* (2013.01); *C07D 413/12* (2013.01); *A61P 25/00* (2018.01)

(58) Field of Classification Search
CPC .. C07D 403/12; C07D 413/12; A61K 31/506; A61P 25/00
See application file for complete search history.

(56) References Cited

U.S. PATENT DOCUMENTS

2015/0166523 A1 6/2015 Araki et al.

FOREIGN PATENT DOCUMENTS

| | | | |
|---|---|---|---|
| EP | 2862855 | A1 | 4/2015 |
| WO | 03051872 | A1 | 6/2003 |
| WO | 2016034882 | A1 | 3/2016 |
| WO | 2017178338 | A1 | 10/2017 |
| WO | 2017178340 | A1 | 10/2017 |
| WO | 2017178343 | A1 | 10/2017 |
| WO | 2017178344 | A1 | 10/2017 |

OTHER PUBLICATIONS

International report on Patentability for PCT/EP2017/058314, dated Nov. 2, 2018.
International Search Report for PCT/EP2017/058312 dated May 24, 2017.
Written Search Report for PCT/EP2017/058312 dated May 4, 2017.
Suzuki, Discovery and invitro and in vivo profiles of N-ethyl-N-[2-[3-(5-fluoro-2-pyridinyl-)-1H-pyrazol-1-yl-ethyl]-2-(2H-1,2,3-triazol-2-yl)-benzamide asa novel class of dual orexin receptor antagonist, Bioorganic and Medicinal Chemistry, 2014.
International Search Report for PCT/EP2017/058314, dated May 19, 2017.
Written Opinion of the Internation Search Authority for PCT/EP2017/058314 dated May 19, 2017.
International Search Report for PCT/EP2017/058315 dated May 9, 2017.
International Search Report and Written Opinion for PCT/EP2017/058320 dated May 24, 2017.

*Primary Examiner* — Bruck Kifle
(74) *Attorney, Agent, or Firm* — David L. Kershner

(57) ABSTRACT

This invention relates to compounds of formula (I), a process for their preparation, pharmaceutical compositions containing them and their use in the treatment of conditions having an association with the orexin sub-type 1 receptor. Ar, $R^1$, $R^2$, $R^3$, $R^4$, $R^5$ have meanings given in the description.

(I)

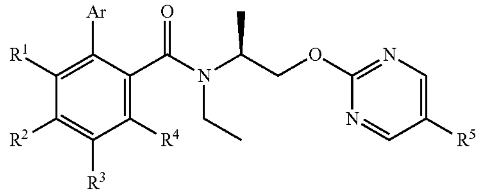

11 Claims, No Drawings

N-[(PYRIMIDINYLOXY)PROPANYL]BENZAMIDES

FIELD OF THE INVENTION

The present invention relates to novel N-[(pyrimidinyloxy)propanyl]benzamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep-wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more). Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8):e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R.

Due to their sleep-inducing effects, dual OX1R and OX2R antagonists are not suitable for treating disorders related to impulse control deficits as seen in addictions such as substance use disorders, personality disorders such as borderline personality disorder, eating disorders such as binge eating disorder, or attention deficit hyperactivity disorder (ADHD). Therefore, it is desirable to provide an OX1R selective antagonist for the treatment of impulse control deficits.

Orexin receptor antagonists of various structural classes are reviewed in Roecker et al. (J. Med. Chem. 2015, 59, 504-530). WO2013/187466, WO2016/034882 and Bioorganic & Medicinal Chemistry 2015, 23, 1260-1275 describe orexin receptor antagonists.

DETAILED DESCRIPTION OF THE INVENTION

The present invention provides novel N-ethyl-N-[(2S)-1-(pyrimidin-2-yloxy)propan-2-yl]-benzamides of formula I

I

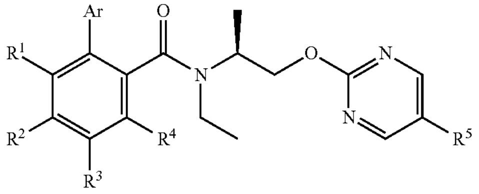

in which

Ar represents

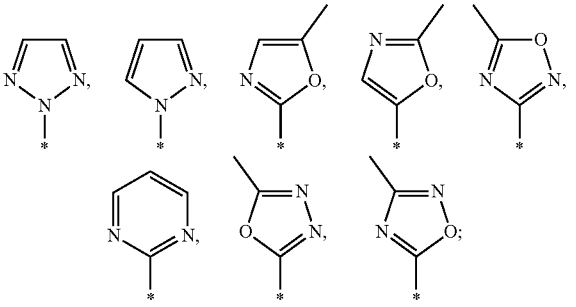

$R^1$ represents hydrogen, fluoro, methyl;

$R^2$ and $R^3$ independently represent hydrogen, fluoro, methyl, —$OCH_3$;

$R^4$ represents hydrogen or fluoro;

$R^5$ represents bromo or —$CF_3$;

or a salt thereof, particularly a physiologically acceptable salt thereof.

In another embodiment, in the general formula I, Ar and $R^5$ have the same meaning as defined in any of the preceding embodiments, and at least two of the substituents $R^1$, $R^2$, $R^3$ and $R^4$ represent hydrogen.

In another embodiment, in the general formula I, Ar, $R^1$, $R^4$ and $R^5$ have the same meaning as defined in any of the preceding embodiments, and $R^2$ represents hydrogen, fluoro, methyl, —$OCH_3$; and $R^3$ represents hydrogen, fluoro, methyl, —$OCH_3$.

In another embodiment, in the general formula I, Ar, $R^4$ and $R^5$ have the same meaning as defined in any of the preceding embodiments, and $R^1$, $R^2$ and $R^3$ independently represent hydrogen or fluoro.

In another embodiment, in the general formula I, Ar, $R^1$, $R^2$, $R^3$ and $R^5$ have the same meaning as defined in any of the preceding embodiments, and $R^4$ represents hydrogen.

In another embodiment, in the general formula I, Ar, $R^1$, $R^2$, $R^3$ and $R^4$ have the same meaning as defined in any of the preceding embodiments, and $R^5$ represents —$CF_3$.

In another embodiment, in the general formula I, $R^1$, $R^2$, $R^3$, $R^4$ and $R^5$ have the same meaning as defined in any of the preceding embodiments, and Ar represents

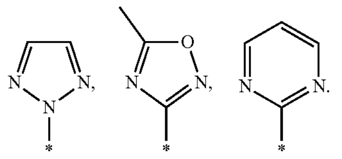

In another embodiment, in the general formula I,
Ar represents

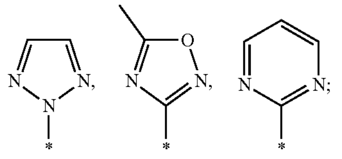

$R^1$, $R^2$ and $R^3$ independently represent hydrogen or fluoro;
$R^4$ represents hydrogen;
$R^5$ represents $—CF_3$.

Compounds of the present invention are potent OX1R antagonists. They are more selective over the OX2R than preferred examples disclosed in WO2013/187466. Compounds of the present invention differ structurally from those disclosed in WO2013/187466 in that they contain a substituted —O-pyrimidyl moiety in place of a Het1-Het2 moiety in which Het2 is phenyl or pyridyl. These structural differences unexpectedly result in an explicit enhancement in selectivity over the OX2R.

Compounds of the present invention differ structurally from Examples 14 and 91 in WO2016/034882 (closest prior art) in that they contain a central N-ethyl-(propan-2-yl) amino moiety in place of the N-methyl-[butan-2-yl]amino moiety or a N-methyl-(propan-2-yl)amino moiety and contain a —O-pyrimidyl instead of the —N-pyrimidyl or —N-pyridyl substituent. These structural differences unexpectedly result either in a marked increase in potency at the OX1R at comparable or higher selectivity over OX2R, or in an explicit enhancement in selectivity over the OX2R at comparable or increased potency at OX1R. Therefore, compounds of the present invention are expected either to be more efficacious in vivo or to have a larger therapeutic window or to demonstrate both characteristics. Either of these qualities results in a better drug safety. A drug compound that is more efficacious may be administered at lower doses thereby reducing the likelihood of OX1R independent side effects. A drug compound that is more selective over OX2R is expected to cause fewer side effects such as drowsiness or sleep. Consequently, compounds of the present invention are expected to be safer and must thus be more viable for human use.

General Definitions

Terms not specifically defined herein should be given the meanings that would be given to them by one skilled in the art in light of the disclosure and the context.

Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays

Abbreviations:

| | |
|---|---|
| IP1 | D-myo-Inositol-1-phosphate |
| IP3 | D-myo-inositol-1,4,5-triphosphate |
| HEPES | 4-(2-hydroxyethyl)-1-piperazineethanesulfonic acid |
| HBSS | Hanks' Balanced Salt Solution |
| BSA | bovine serum albumin |
| DMSO | dimethyl sulfoxide |
| CHO | Chinese hamster ovary |

Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay.) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:

A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 10000 cells/25 μL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM and/or 50 nM) dissolved in assay buffer is added to the assay plate. The assay plate is incubated for 60 minutes at 37° C. Then 5 μl per well of Anti-IP1-Cryptate Tb solution and 5 μl per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}$=$EC_{50}$ agonist, n=Hill slope agonist).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx2 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 5000 cells/25 μL per well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM) dissolved in assay buffer is added to the assay plate. The assay plate is incubated for 60 minutes at 37° C. Then 5 μl per well of Anti-IP1-Cryptate Tb solution and 5 μl per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $10_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}$=$EC_{50}$ agonist, n=Hill slope agonist) (see P. Leff, I. G. Dougall, Trends Pharmacol. Sci. 1993, 14(4), 110-112).

Kb values from Assay A (OX1R) and Assay B (OX2R) can then provide a selectivity ratio which is independent of the agonist (Orexin A) concentration.

Biological Data

Comparison of Assays A and B with the Assays Described in WO2013/187466

Assays described in WO2013/187466 differ from assays A and B in:

- The technology and readout: fluorescence measurement of intracellular $Ca^{2+}$ changes (WO2013/187466) instead of luminescence measurement of IP1 (assays A and B)
- OX1R and OX2R overexpressing cell lines used for the assays described in WO2013/187466 are of different origin as cell lines used for assays A and B
- Use of modified orexin A (2 amino acids substituted) as agonist instead of orexin A
- Agonist concentration of 300 pM used for the OX1R assay and 3 nM for the OX2R assay (EC75 vs. EC100; according to Okumura T. et al., Biochemical and Biophysical Research Communications, 2001) (WO2013/187466). $IC_{50}$ values that have been reported are dependent on the agonist concentration. Selectivity ratios calculated from these $IC_{50}$ values cannot be compared with the selectivity ratios calculated from the agonist concentration independent Kb values obtained from assay A and B.

Due to these differences between the assays, a direct comparison has to be established. Therefore, examples 69, 70 (the most selective ones) and 5 (one of the most potent ones) described in WO2013/187466 are tested in assays A and B so as to be directly compared with compounds of the present invention (see Table 1).

TABLE 1
In vitro potencies of compounds of WO2013/187466 as reported therein versus as determined in the Assays A and B (described above)
| Structure Example # in WO2013/187466 | As described in WO2013/187466 OX1R $IC_{50}$ [nM] | OX2R $IC_{50}$ [nM] | OX2R $IC_{50}$/ OX1R $IC_{50}$ | As determined in Assays A and B OX1R Kb [nM] (Orexin A concentration used) | OX2R Kb [nM] (0.5 nM Orexin A concentration) | OX2R Kb/ OX1R Kb |
|---|---|---|---|---|---|---|
| 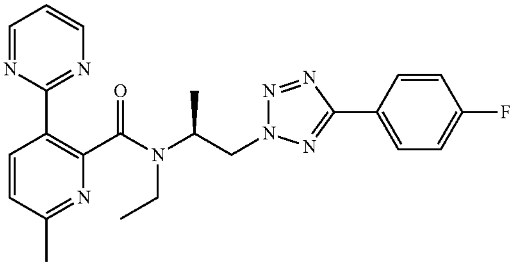 Example 69 | 1.6 | 1896 | 1185 | 2.25 (0.5 nM) | 98 | 43 |
| 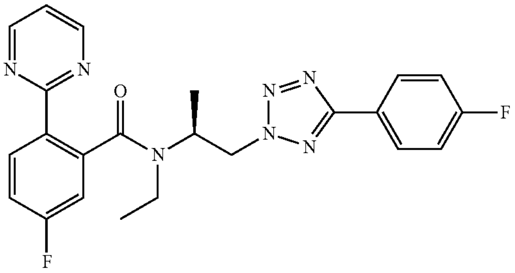 Example 70 | 1.1 | 452 | 411 | 0.72 (50 nM) | 29 | 40 |
| 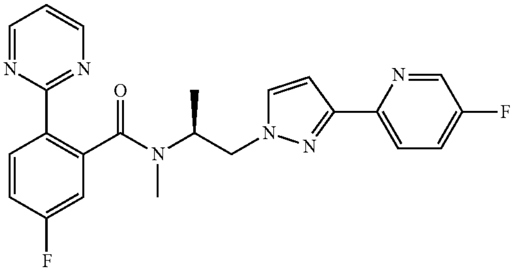 Example 5 | 0.5 | 76 | 152 | 0.94 (50 nM) | 28 | 30 |

TABLE 2

In vitro potencies of the structurally closest prior art compounds (Example 14 and 91) WO2016/034882 as reported therein:

| Structure<br>Example # in WO2016/034882 | OX1R | OX2R | OX2R $IC_{50}$/<br>OX1R $IC_{50}$ |
|---|---|---|---|
| | As described in WO2016/034882 (Table 1, page 178) | | |
| 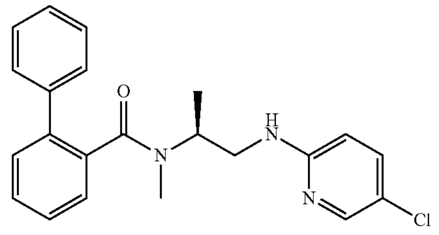<br>Example 14 | Table 1:<br>$pIC_{50}$ = 8.3<br>corresponds to<br>$IC_{50}$ = 5.0 nM<br>Table 2:<br>$pIC_{50}$ = 7.8<br>corresponds to<br>$IC_{50}$ = 16 nM<br>Table 3:<br>not reported | Table 1:<br>$pIC_{50}$ = 6.8<br>corresponds to<br>$IC_{50}$ = 158 nM<br>Table 2:<br>$pIC_{50}$ = 7.2<br>corresponds to<br>$IC_{50}$ = 63 nM<br>Table 3:<br>not reported | Table 1:<br>32<br>Table 2:<br>4 |
| 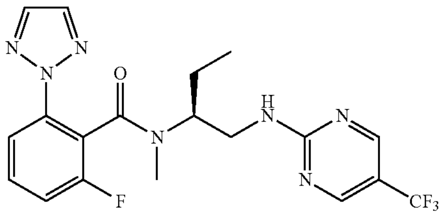<br>Example 91 | Table 1 and 2:<br>not reported<br>Table 3:<br>$pIC_{50}$ = 7.6<br>corresponds to<br>$IC_{50}$ = 25 nM | Table 1 and 2:<br>not reported<br>Table 3:<br>$pIC_{50}$ <5.1<br>corresponds to<br>$IC_{50}$ = >7950 nM | Table 3:<br>>318 |

Table 3 shows a comparison of biological data on the OX1R and OX2R potencies of the compounds of the present invention with the closest prior art compounds in WO2016/034882.

Examples 1, 2, 5, 7, 10, 11, 13, 14, 20, 22, 24, 30, 34 and 35 of the present invention differ structurally from Example 91 in WO2016/034882, the closest prior art compound, in that they contain a) a central N-ethyl-(propan-2-yl)amino moiety in place of the N-methyl-[butan-2-yl]amino moiety, and b) a —O-pyrimidyl instead of the —N-pyrimidyl substituent. Further, the phenyl group may have a different substitution pattern.

In Examples 1, 7 and 20, the fluoro substituent of the phenyl group is in a different position than in Example 91 in WO2016/034882. In Examples 35 and 22, the phenyl group bears an additional fluoro substituent. These structural differences unexpectedly result in Examples 1, 7, 20, 35, 22 being more selective for OX1R over OX2R (selectivity ratio OX2R Kb/OX1R Kb) as compared to Example 91 in WO2016/034882.

In Example 2, the phenyl group carries two methyl groups. These structural differences lead to an increase in OX1R potency compared to Example 91 in WO2016/034882.

In Examples 5, 10, 11, 13, 14, 24, and 30, the phenyl group is unsubstituted or substituted with a methoxy, or one or two methyl groups instead of the fluoro substituent in Example 91 in WO2016/034882. These structural differences unexpectedly result in an increase in both OX1R potency and OX1R selectivity compared to Example 91 in WO2016/034882.

In Example 34, the phenyl group contains a methyl group in addition to the fluoro substituent in Example 91 in WO2016/034882. This structural difference unexpectedly leads to an increase in OX1R potency and an increase in OX1R selectivity compared to Example 91 in WO2016/034882.

Examples 8, 15, 18, 19, 21, 23, 31, and 36 of the present invention differ structurally from Example 91 in WO2016/034882, the closest prior art compound, in that they a) contain a central N-ethyl-(propan-2-yl)amino moiety in place of the N-methyl-[butan-2-yl]amino moiety and b) contain a —O-pyrimidyl instead of the —N-pyrimidyl substituent. They further have a differently substituted phenyl group: They contain a pyrazoyl, oxadiazoyl, or oxazoyl instead of the triazoyl, and further the phenyl group is unsubstituted or substituted with a methyl, a fluoro in a different position than in Example 91 in WO2016/034882. These structural differences lead to an increase in OX1R selectivity compared to Example 91 in WO2016/034882.

Example 29 of the present invention differs structurally from Example 91 in WO2016/034882, the closest prior art compound, in that it contains a) a central N-ethyl-(propan-2-yl)amino moiety in place of the N-methyl-[butan-2-yl]amino moiety and b) a —O-pyrimidyl instead of the —N-pyrimidyl substituent. It further contains the fluoro substituent on the phenyl group in a different position as compared to Example 91 in WO2016/034882, and contains a bromo substituted pyrimidine rather than the $CF_3$-substituted pyrimidine. These structural differences unexpectedly lead to an increase in OX1R selectivity compared to Example 91 in WO2016/034882.

Examples 32, 28, and 25 of the present invention differ structurally from Example 14 in WO2016/034882, the closest prior art compound, in that they contain a) a central N-ethyl-(propan-2-yl)amino moiety in place of the N-methyl-[prop-2-yl]amino moiety and b) a —O-pyrimidyl instead of the —N-pyridyl substituent. They further contain a pyrimidine instead of the second phenyl group. Examples 32 and 25 further contain a fluoro substituent on the phenyl group. These structural differences unexpectedly result in an increase in OX1R selectivity compared to Example 14 in WO2016/034882.

TABLE 3
Comparison of biological data of the compounds of the present invention with the closest prior art compounds in WO2016/034882
| Example | Structure | Assay A OX1R Kb [nM] (Orexin A concentration) | Assay B OX2R Kb [nM] (0.5 nM Orexin A concentration) | OX2RKb/ OX1R Kb |
|---|---|---|---|---|
| Ex 91 in WO2016/ 034882 | 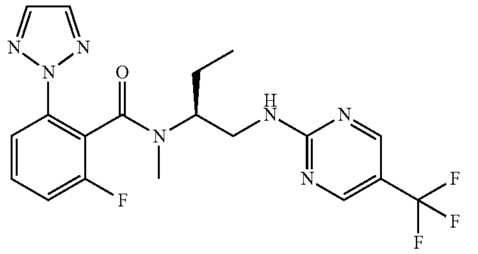 [SMILES: CC[C@@H](CNc1ncc(C(F)(F)F)cn1)N(C)C(=O)c1c(F)cccc1-n1nccn1] | 3.63 (0.5 nM) | 313 | 86 |
| 1 | 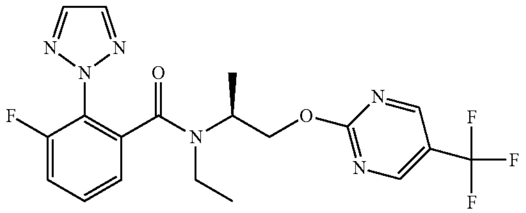 [SMILES: CCN(C(=O)c1cccc(F)c1-n1nccn1)[C@@H](C)COc1ncc(C(F)(F)F)cn1] | 1.7 (0.5 nM) 2.5 (50 nM) | 425 | 250 170 |
| 7 | 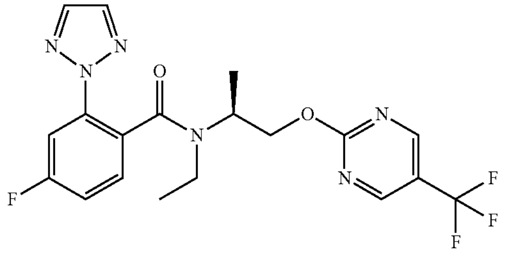 [SMILES: CCN(C(=O)c1ccc(F)cc1-n1nccn1)[C@@H](C)COc1ncc(C(F)(F)F)cn1] | 4.5 (0.5 nM) | 902 | 201 |
| 20 | 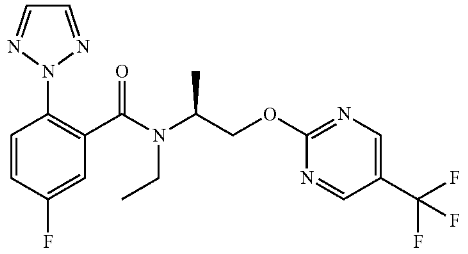 | 2.6 (0.5 nM) | 803 | 309 |
| 35 | 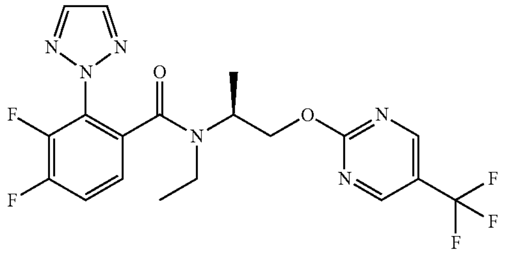 [SMILES: CCN(C(=O)c1ccc(F)c(F)c1-n1nccn1)[C@@H](C)COc1ncc(C(F)(F)F)cn1] | 2.5 (0.5 nM) | 455 | 182 |

TABLE 3-continued
Comparison of biological data of the compounds of the present invention with the closest prior art compounds in WO2016/034882
| Example | Structure | Assay A OX1R Kb [nM] (Orexin A concentration) | Assay B OX2R Kb [nM] (0.5 nM Orexin A concentration) | OX2RKb/ OX1R Kb |
|---|---|---|---|---|
| 22 | 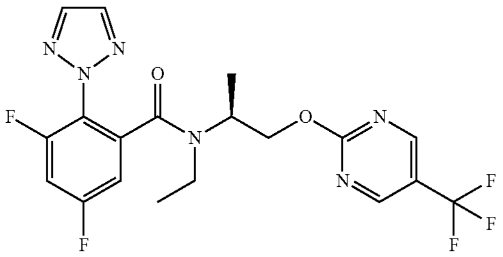 [SMILES: CCN(C(=O)c1cc(F)cc(F)c1-n1nccn1)[C@@H](C)COc1ncc(C(F)(F)F)cn1] | 3.6<br>(0.5 nM) | 1461 | 406 |
| 2 | 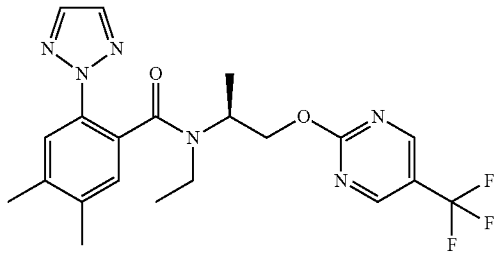 [SMILES: CCN(C(=O)c1cc(C)c(C)cc1-n1nccn1)[C@@H](C)COc1ncc(C(F)(F)F)cn1] | 0.39<br>(50 nM) | 34 | 87 |
| 5 | 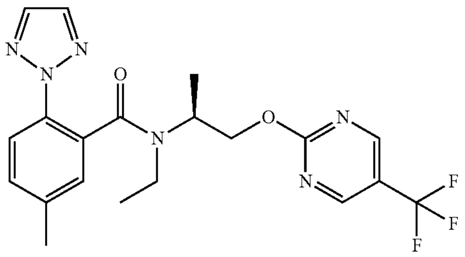 [SMILES: CCN(C(=O)c1cc(C)ccc1-n1nccn1)[C@@H](C)COc1ncc(C(F)(F)F)cn1] | 1.0<br>(0.5 nM)<br>1.1<br>(50 nM) | 156 | 156<br>142 |
| 10 | 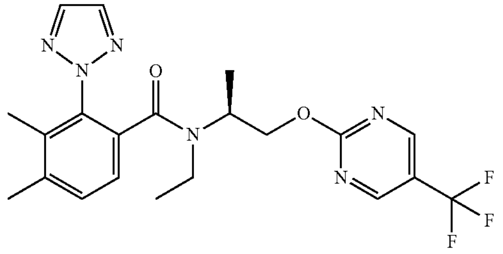 [SMILES: CCN(C(=O)c1ccc(C)c(C)c1-n1nccn1)[C@@H](C)COc1ncc(C(F)(F)F)cn1] | 0.65<br>(50 nM) | 565 | 869 |
| 11 | 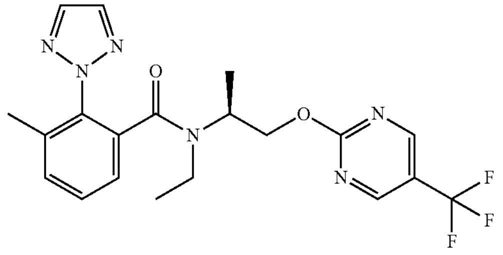 [SMILES: CCN(C(=O)c1cccc(C)c1-n1nccn1)[C@@H](C)COc1ncc(C(F)(F)F)cn1] | 1.3<br>(0.5 nM)<br>1.4<br>(50 nM) | 160 | 123<br>114 |

TABLE 3-continued
| Comparison of biological data of the compounds of the present invention with the closest prior art compounds in WO2016/034882 | | | | |
|---|---|---|---|---|
| Example | Structure | Assay A OX1R Kb [nM] (Orexin A concentration) | Assay B OX2R Kb [nM] (0.5 nM Orexin A concentration) | OX2RKb/ OX1R Kb |
| 13 | 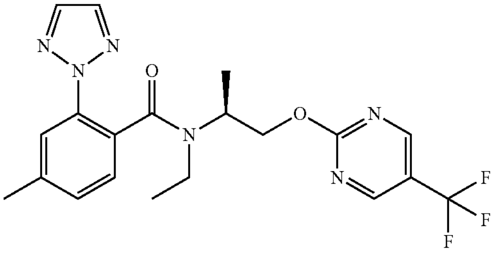 [SMILES: CCN(C(=O)c1ccc(C)cc1-n1nccn1)[C@@H](C)COc1ncc(C(F)(F)F)cn1] | 0.5 (0.5 nM) 0.38 (50 nM) | 142 | 284 374 |
| 14 | 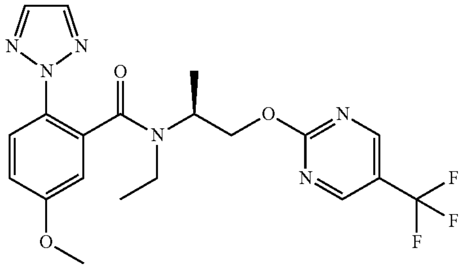 [SMILES: CCN(C(=O)c1cc(OC)ccc1-n1nccn1)[C@@H](C)COc1ncc(C(F)(F)F)cn1] | 0.97 (0.5 nM) 1.21 (50 nM) | 253 | 261 209 |
| 30 | 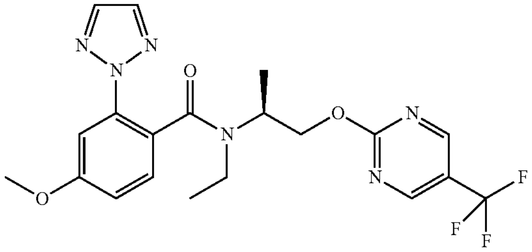 [SMILES: CCN(C(=O)c1ccc(OC)cc1-n1nccn1)[C@@H](C)COc1ncc(C(F)(F)F)cn1] | 1.8 (0.5 nM) | 579 | 322 |
| 34 | 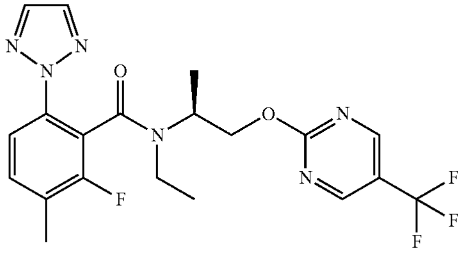 [SMILES: CCN(C(=O)c1c(-n2nccn2)ccc(C)c1F)[C@@H](C)COc1ncc(C(F)(F)F)cn1] | 1.8 (0.5 nM) | 431 | 239 |
| 24 | 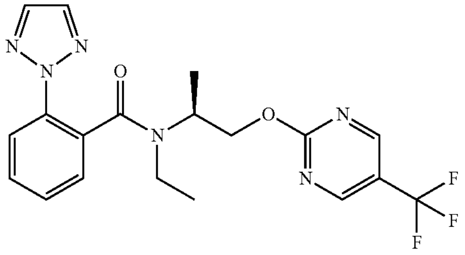 [SMILES: CCN(C(=O)c1ccccc1-n1nccn1)[C@@H](C)COc1ncc(C(F)(F)F)cn1] | 1.8 (0.5 nM) 2.6 (50 nM) | 237 | 132 91 |

TABLE 3-continued
Comparison of biological data of the compounds of the present invention with the closest prior art compounds in WO2016/034882
| Example | Structure | Assay A OX1R Kb [nM] (Orexin A concentration) | Assay B OX2R Kb [nM] (0.5 nM Orexin A concentration) | OX2RKb/ OX1R Kb |
|---|---|---|---|---|
| 8 | 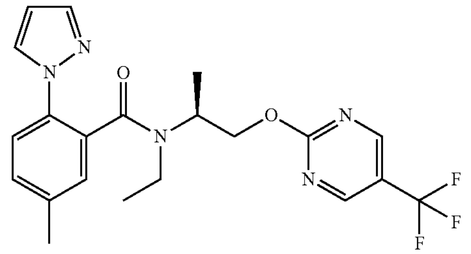 [SMILES: CCN(C(=O)c1cc(C)ccc1-n1cccn1)[C@@H](C)COc1ncc(C(F)(F)F)cn1] | 2.2 (0.5 nM) | 502 | 228 |
| 15 | 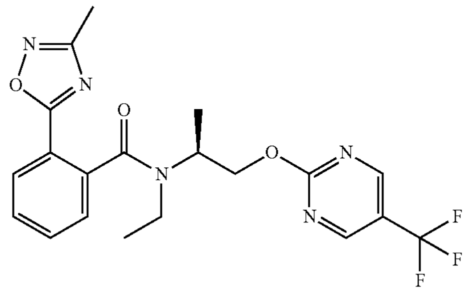 [SMILES: CCN(C(=O)c1ccccc1-c1nc(C)no1)[C@@H](C)COc1ncc(C(F)(F)F)cn1] | 7.8 (0.5 nM) | 999 | 128 |
| 18 | 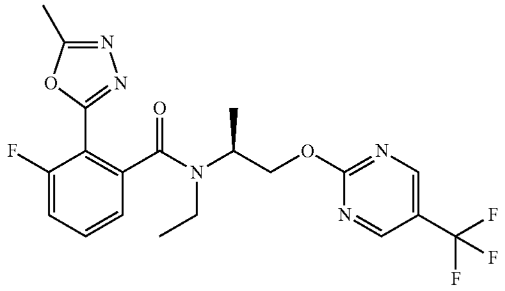 [SMILES: CCN(C(=O)c1cccc(F)c1-c1nnc(C)o1)[C@@H](C)COc1ncc(C(F)(F)F)cn1] | 16 (0.5 nM) | 6637 | 415 |
| 19 | 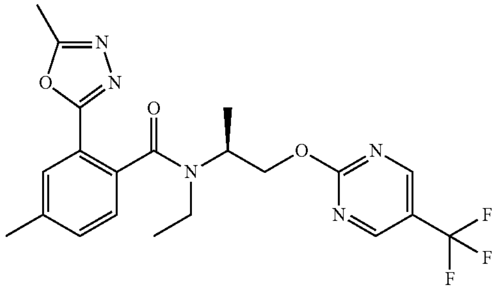 [SMILES: CCN(C(=O)c1ccc(C)cc1-c1nnc(C)o1)[C@@H](C)COc1ncc(C(F)(F)F)cn1] | 7.3 (0.5 nM) | 6638 | 909 |
| 21 | 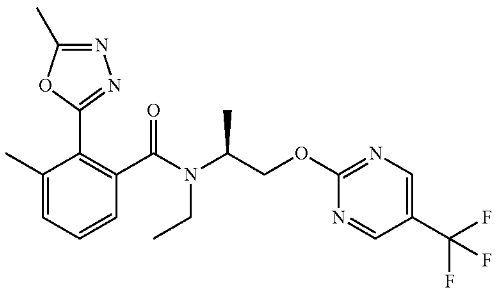 [SMILES: CCN(C(=O)c1cccc(C)c1-c1nnc(C)o1)[C@@H](C)COc1ncc(C(F)(F)F)cn1] | 2.0 (0.5 nM) 1.9 (50 nM) | 540 | 270 284 |

TABLE 3-continued
Comparison of biological data of the compounds of the present invention with the closest prior art compounds in WO2016/034882
| Example | Structure | Assay A OX1R Kb [nM] (Orexin A concentration) | Assay B OX2R Kb [nM] (0.5 nM Orexin A concentration) | OX2RKb/ OX1R Kb |
|---|---|---|---|---|
| 23 | 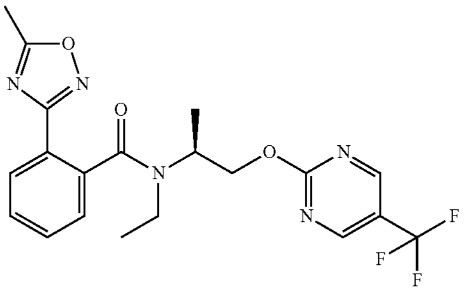 [SMILES: CCN(C(=O)c1ccccc1-c1noc(C)n1)[C@@H](C)COc1ncc(C(F)(F)F)cn1] | 2.1 (0.5 nM) | 435 | 207 |
| 31 | 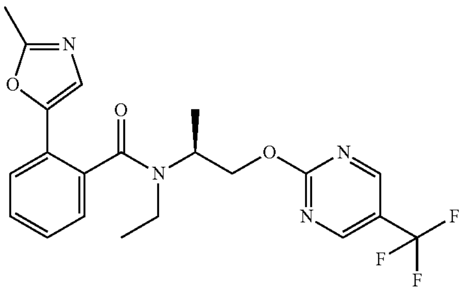 [SMILES: CCN(C(=O)c1ccccc1-c1cnc(C)o1)[C@@H](C)COc1ncc(C(F)(F)F)cn1] | 6.0 (0.5 nM) | 746 | 124 |
| 36 | 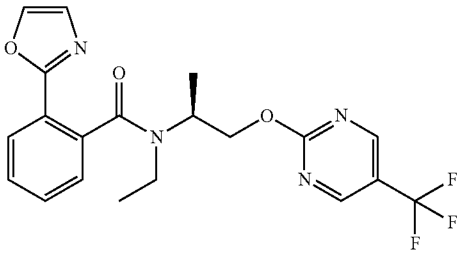 [SMILES: CCN(C(=O)c1ccccc1-c1ncco1)[C@@H](C)COc1ncc(C(F)(F)F)cn1] | 3.2 (0.5 nM) | 511 | 160 |
| 29 | 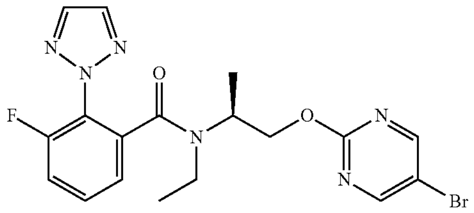 [SMILES: CCN(C(=O)c1cccc(F)c1-n1nccn1)[C@@H](C)COc1ncc(Br)cn1] | 2.0 (0.5 nM) | 350 | 178 |
| Ex 14 in WO2016/ 034882 | 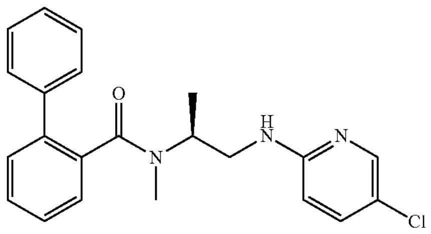 [SMILES: C[C@@H](CNc1ccc(Cl)cn1)N(C)C(=O)c1ccccc1-c1ccccc1] | 0.171 (50 nM) | 4.7 | 27 |

TABLE 3-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb |
|---|---|---|---|---|
| 32 | 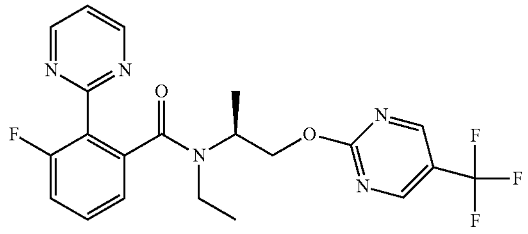 [SMILES: CCN(C(=O)c1cccc(F)c1-c1ncccn1)[C@@H](C)COc1ncc(C(F)(F)F)cn1] | 0.61 (0.5 nM) 0.46 (50 nM) | 188 | 308 408 |
| 28 | 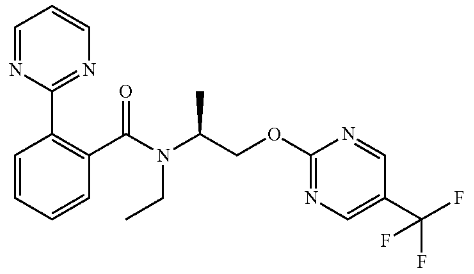 [SMILES: CCN(C(=O)c1ccccc1-c1ncccn1)[C@@H](C)COc1ncc(C(F)(F)F)cn1] | 0.62 (0.5 nM) 0.74 (50 nM) | 176 | 284 238 |
| 25 | 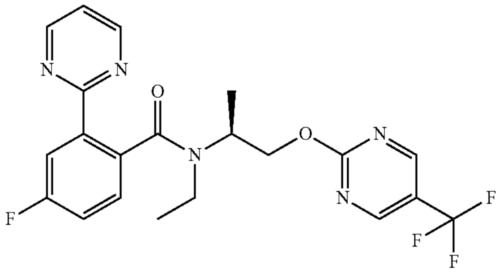 [SMILES: CCN(C(=O)c1ccc(F)cc1-c1ncccn1)[C@@H](C)COc1ncc(C(F)(F)F)cn1] | 0.81 (0.5 nM) 1.4 (50 nM) | 272 | 336 194 |

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

- Antidepressants
- Mood stabilizers
- Antipsychotics
- Anxiolytics
- Antiepileptic drugs
- Sleeping agents
- Cognitive enhancer
- Stimulants
- Non-stimulant medication for attention deficit hyperactivity disorder
- Additional psychoactive drugs.

General Synthetic Methods

The invention also provides a process for making compounds of Formula (I). Unless specified otherwise, $R^1$, $R^2$, $R^3$, $R^4$, $R^5$ and Ar in the formulas below shall have the meaning as defined for formula I in the detailed description of the invention above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), liquid chromatography-mass spectrometry (LC-MS) if desired, and intermediates and products may be purified by chromatography and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Compounds of Formula (I) can be synthesized by the method illustrated in Scheme 1:

Scheme 1

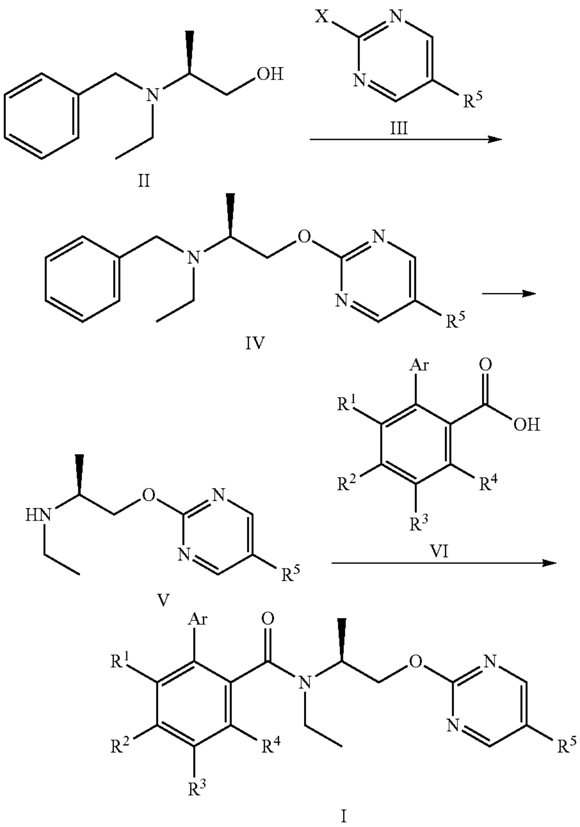

As shown in scheme 1, reacting the alcohol of formula II with a halo pyrimidine III (X=halide) in a nucleophilic aromatic substitution reaction, in a suitable solvent such as dioxane, THF or DMF and in the presence of a suitable base such as potassium tert-butoxide or NaH, provides an ether of formula IV. Debenzylation reactions are described in ‘Protective Groups in Organic Synthesis’, 3' edition, T. W. Greene and P. G. M. Wuts, Wiley-Interscience (1999). Debenzylation of compound IV using 1-chloroethylchloroformate as a hydrogenating reagent may be used in a suitable solvent such as 1,2-dichloroethane to provide an amine of formula V.

Peptide coupling reactions known to the person skilled in the art (see for example M. Bodanszky, 1984, The Practice of Peptide Synthesis, Springer-Verlag) can be applied to react the secondary amine of formula V with a carboxylic acid of formula VI to yield a compound of formula I. For example, amine V and carboxylic acid VI in a suitable solvent such as acetonitrile or DMF in the presence of a suitable base such as DIPEA yields upon treatment with the coupling agent 2-chloro-4,5-dihydro-1,3-dimethyl-1H-imidazolium hexafluorophosphate (CIP) or 1-[bis(dimethylamino)methylene]-1H-1,2,3-triazolo[4,5-b]pyridinium 3-oxid hexafluorophosphate (HATU) a compound of formula I.

Alternatively, compounds of Formula I can be synthesized as illustrated in Scheme 2:

Scheme 2

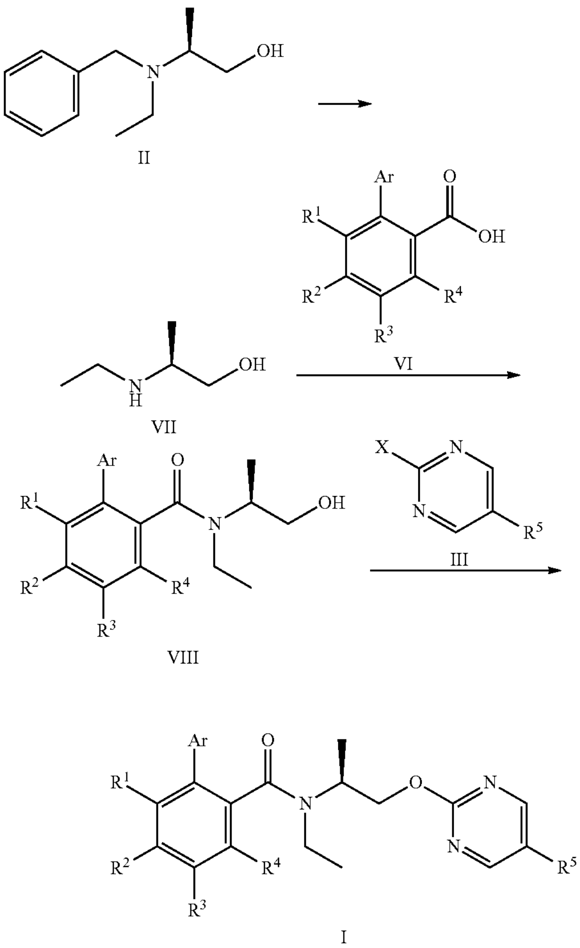

II

VI

VII

VIII

III

I

Debenzylation reactions are described in ‘Protective Groups in Organic Synthesis’, 3' edition, T. W. Greene and P. G. M. Wuts, Wiley-Interscience (1999). Debenzylation of compound II in a suitable solvent such as MeOH, with under a pressure of hydrogen in the presence of a suitable catalyst such as Pd/C results in a secondary amine of formula VII.

Peptide coupling reactions known to the person skilled in the art (see for example M. Bodanszky, 1984, The Practice of Peptide Synthesis, Springer-Verlag) can be applied to react the secondary amine of formula VII with a carboxylic acid of formula VI to yield a compound of formula VIII. For example, carboxylic acid VI in a suitable solvent such as DCM, DMF and toluene upon treatment with thionyl chloride or oxalyl chloride yields an acid chloride which is then treated with an amine of formula VII, in a suitable solvent such as DCM and THF, in the presence of a suitable base such as TEA, to provide a compound of formula VIII. Other peptide coupling reagents such as HATU in a suitable solvent such as DMF in the presence of a suitable base such as DIPEA may be used.

Reacting the alcohol of formula VIII with a halo pyrimidine III (X=halide) in a nucleophilic aromatic substitution reaction, in a suitable solvent such as dioxane, DMSO or DMF and in the presence of a suitable base such as potassium tert-butoxide or NaH, provides a compound of formula I. Alternatively, the alcohol of formula VIII can be reacted with a hydroxy pyrimidine of formula III (X═OH) in a Mitsunobu reaction in the presence of diethylazodicarboxylate (DEAD) or diisopropylazodicarboxylate (DIAD) and in the presence of triphenylphosphine to provide a compound of formula I.

Alternatively, an alcohol of formula VIII can be synthesized as illustrated in Scheme 3:

Scheme 3

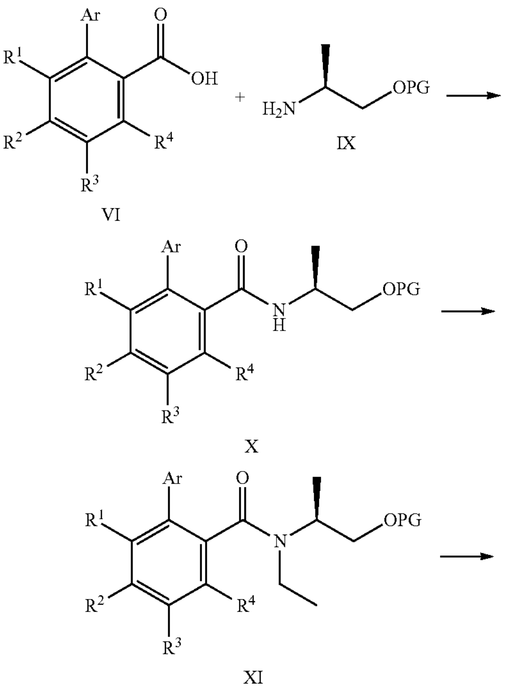

VI

IX

X

XI

-continued

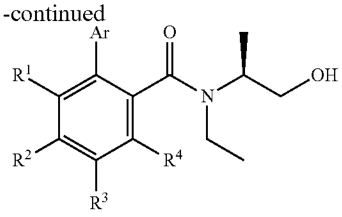

VIII

Peptide coupling reactions known to the person skilled in the art (see for example M. Bodanszky, 1984, The Practice of Peptide Synthesis, Springer-Verlag) can be applied to react a secondary amine of formula IX, in which the protecting group (PG) may be a tert-butyl-dimethylsilyl group, with a carboxylic acid of formula VI to yield a compound of formula X. For example, a peptide coupling reagents such as TBTU or HATU in a suitable solvent such as DMF in the presence of a suitable base such as DIPEA may be used. Alkylation of the amide X using a suitable alkylation agent such as ethyl iodide in a suitable solvent such as DMF and a suitable base such as potassium tert-butoxide yields amide XI.

Deprotection reactions described in 'Protective Groups in Organic Synthesis', 3' edition, T. W. Greene and P. G. M. Wuts, Wiley-Interscience (1999) can be applied in providing alcohol VIII from compound XI. For example tetra-n-butylammonium fluoride in a suitable solvent such as THF may be used.

Intermediate carboxylic acids V are commercially available or they can be synthesized according or in analogy to methods described in the literature.

EXPERIMENTAL SECTION

List of Abbreviations

RT room temperature
CIP 2-chloro-4,5-dihydro-1,3-dimethyl-1H-imidazolium hexafluorophosphate
dppf 1,1'-bis(diphenylphosphanyl)ferrocene
ESI-MS electrospray ionisation mass spectrometry
aq. aqueous
MS mass spectrometry
MeOH methanol
EtOH ethanol
EA ethyl acetate
DMF N,N-dimethylformamide
DMSO dimethyl sulfoxide
DCM dichloromethane
TEA triethylamine
THF tetrahydrofuran
DIPEA N,N-diisopropylethylamine
HATU 1-[bis(dimethylamino)methylene]-1H-1,2,3-triazolo[4,5-b]pyridinium 3-oxid hexafluorophosphate
TBTU O-(benzotriazol-1-yl)-N,N,N',N'-tetramethyl-uronium tetrafluoroborate
Rt retention time
h hour(s)
min minutes
sat. saturated
ACN acetonitrile
TFA trifluoroacetic acid
M molarity
N normality
HPLC high-performance liquid chromatography HPLC-MS high-performance liquid chromatography-mass spectrometry
LC-MS liquid chromatography-mass spectrometry
TLC thin layer chromatography
DIAD diisopropyl azodicarboxylate
DEAD diethyl azodicarboxylate
HPLC-Methods:
Method Name: A
Column: Venusil XBP-C18, 2.1×50 mm, 5 μm
Column Supplier: Agela Technologies

| Gradient/ Solvent Time [min] | % Sol [$H_2O$, 0.0375% TFA] | % Sol [ACN, 0.018% TFA] | Flow [mL/min] | Temp [° C.] |
|---|---|---|---|---|
| 0.00 | 90 | 10 | 0.8 | 50 |
| 0.40 | 90 | 10 | 0.8 | 50 |
| 3.40 | 0 | 100 | 0.8 | 50 |
| 3.85 | 0 | 100 | 0.8 | 50 |
| 3.86 | 90 | 10 | 0.8 | 50 |
| 4.50 | 90 | 10 | 0.8 | 50 |

Method Name: B
Column: Sunfire C18, 2.1×30 mm, 2.5 μm
Column Supplier: Waters

| Gradient/ Solvent Time [min] | % Sol [$H_2O$, 0.1% TFA] | % Sol [ACN] | Flow [mL/min] | Temp [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method Name: C
Column: Chromolith Flash RP-18e 25-2 mm
Column Supplier: Merck

| Gradient/ Solvent Time [min] | % Sol [$H_2O$, 0.0375% TFA] | % Sol [ACN, 0.018% TFA] | Flow [mL/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

Method Name: D
Column: XBridge BEH Phenyl, 2.1×30 mm, 1.7 μm
Column Supplier: Waters

| Gradient/ Solvent Time [min] | % Sol [$H_2O$, 0.1% $NH_3$] | % Sol [Acetonitril] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: E
Column: XBridge C18, 4.6×30 mm, 3.5 μm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: F
Column: XBridge C18, 3×30 mm, 2.5 μm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: H
Column: Sunfire C18, 2.1×30 mm, 2.5 μm
Column Supplier: Waters

| Gradient/Solvent Time [min] | % Sol [$H_2O$, 0.1% TFA] | % Sol [ACN] | Flow [mL/min] | Temp [° C.] |
|---|---|---|---|---|
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method Name: J
Column: Acquity BEH C18, 2.1×50 mm, 1.7 μm
Column Supplier: Waters

| Gradient/Solvent Time [min] | % Sol [$H_2O$, 0.1% TFA] | % Sol [ACN, 0.1% TFA] | Flow [mL/min] | Temp [° C.] |
|---|---|---|---|---|
| 0.0 | 3.0 | 97.0 | 0.6 | 25° C. |
| 0.4 | 3.0 | 97.0 | 0.6 | 25° C. |
| 3.2 | 98.0 | 2.0 | 0.6 | 25° C. |
| 3.8 | 98.0 | 2.0 | 0.6 | 25° C. |
| 4.2 | 3.0 | 97.0 | 0.6 | 25° C. |
| 4.5 | 3.0 | 97.0 | 0.6 | 25° C. |

Method Name: K
Column: Acquity BEH C18, 2.1×50 mm, 1.7 μm
Column Supplier: Waters

| Gradient/Solvent Time [min] | % Sol [H2O, 0.1% TFA] | % Sol [ACN, 0.1% TFA] | Flow [mL/min] | Temp [° C.] |
|---|---|---|---|---|
| 0.0 | 97.0 | 3.0 | 0.55 | 35 |
| 0.4 | 97.0 | 3.0 | 0.55 | 35 |
| 3.2 | 2.0 | 98.0 | 0.55 | 35 |
| 3.8 | 2.0 | 98.0 | 0.55 | 35 |
| 4.2 | 2.0 | 98.0 | 0.55 | 35 |
| 4.5 | 97.0 | 3.0 | 0.55 | 35 |

Method Name: L
Column: XBridge BEH C18, 2.1×30 mm, 1.7 μm
Column Sunnlier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: M
Column: BEH C18 1.7 μm 2.1×50 mm
Column Supplier: Waters

| Gradient/Solvent Time [min] | % Sol [90% $H_2O$ + 10% ACN + $NH_4COOH$ 5 mM] | % Sol [90% ACN + 10% $H_2O$] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: N
Column: Xselect CSH, 2.5 μm, 4.6×50 mm
Column Supplier: Waters

| Gradient/Solvent Time [min] | % Sol [90% $H_2O$ + 10% ACN + 0.1% HCOOH] | % Sol [90% ACN + 10% $H_2O$ + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: O
Column: Synergi Hydro RP100A, 2.5 μm, 3×50 mm
Column Supplier: Phenomenex

| Gradient/Solvent Time [min] | % Sol [90% $H_2O$ + 10% ACN + 5 mM $NH_4COOH$] | % Sol [90% ACN + 10% $H_2O$] | Flow [mL/min] | Temp [° C.] |
|---|---|---|---|---|
| 0.00 | 100 | 0 | 1.2 | RT |
| 4.00 | 0 | 100 | 1.2 | RT |
| 5.30 | 0 | 100 | 1.2 | RT |
| 5.50 | 100 | 0 | 1.2 | RT |
| 6.00 | 100 | 0 | 1.2 | RT |

Method Name: P
Column: Sunfire C18, 3.0×30 mm, 2.5 μm
Column Supplier: Waters

| Gradient/Solvent Time [min] | % Sol [H2O, 0.1% TFA] | % Sol [ACN] | Flow [mL/min] | Temp [° C.] |
|---|---|---|---|---|
| 0.0 | 98.0 | 2.0 | 2.0 | 60 |
| 1.2 | 0.0 | 100.0 | 2.0 | 60 |
| 1.4 | 0.0 | 100.0 | 2.0 | 60 |

Method Name: Q
Column: Atlantis dC18 5 μm 4.6×50 mm, Temp 35° C.
Column Supplier: Waters

| Gradient/ Solvent Time [min] | % Sol [90% $H_2O$ + 10% ACN + 0.05% TFA] | % Sol [90% ACN + 10% $H_2O$] | Flow [mL/min] | Temp [° C.] |
|---|---|---|---|---|
| 0.00 | 100 | 0 | 1.3 | 35 |
| 0.70 | 100 | 0 | 1.3 | 35 |
| 4.5 | 0 | 100 | 1.3 | 35 |
| 5.80 | 0 | 100 | 1.3 | 35 |
| 6.00 | 100 | 0 | 1.3 | 35 |

Method Name: R
Column: Luna-C18 5 μm, 2.0*50 mm
Column Supplier: Phenomenex

| Gradient/ Solvent Time [min] | % Sol [$H_2O$, 0.0375% TFA] | % Sol [ACN, 0.018% TFA] | Flow [mL/min] | Temp [° C.] |
|---|---|---|---|---|
| 0.00 | 99 | 1 | 0.8 | 40 |
| 0.40 | 99 | 1 | 0.8 | 40 |
| 3.40 | 0 | 100 | 0.8 | 40 |
| 3.85 | 0 | 100 | 0.8 | 40 |
| 3.86 | 99 | 1 | 0.8 | 40 |
| 4.50 | 99 | 1 | 0.8 | 40 |

Method Name: S
Column: Luna-C18 3 μm, 2.0*30 mm
Column Supplier: Phenomenex

| Gradient/ Solvent Time [min] | % Sol [$H_2O$, 0.0375% TFA] | % Sol [ACN, 0.018% TFA] | Flow [mL/min] | Temp [° C.] |
|---|---|---|---|---|
| 0.00 | 90 | 10 | 1.0 | 40 |
| 1.15 | 20 | 80 | 1.0 | 40 |
| 1.55 | 20 | 80 | 1.0 | 40 |
| 1.56 | 90 | 10 | 1.0 | 40 |
| 2.00 | 90 | 10 | 1.0 | 40 |

Method Name: T
Column: Luna-C18 3 μm, 2.0*30 mm
Column Supplier: Phenomenex

| Gradient/ Solvent Time [min] | % Sol [$H_2O$, 0.0375% TFA] | % Sol [ACN, 0.018% TFA] | Flow [mL/min] | Temp [° C.] |
|---|---|---|---|---|
| 0.00 | 100 | 0 | 1.0 | 40 |
| 1.60 | 40 | 60 | 1.0 | 40 |
| 1.65 | 40 | 60 | 1.0 | 40 |
| 1.66 | 100 | 0 | 1.0 | 40 |
| 2.20 | 100 | 0 | 1.0 | 40 |

Method Name: U
Column: XBridge BEH C18, 2.1×30 mm, 1.7 μm
Column Supplier: Waters

| Gradient/Solvent Time [min] | % Sol [H2O, 0.1% TFA] | % Sol [ACN] | Flow [mL/min] | Temp [° C.] |
|---|---|---|---|---|
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method Name: V
Column: Sunfire C18, 3.0×30 mm, 2.5 μm
Column Supplier: Waters

| Gradient/Solvent Time [min] | % Sol [H2O, 0.1% TFA] | % Sol [ACN, 0.08% TFA] | Flow [mL/min] | Temp [° C.] |
|---|---|---|---|---|
| 0.0 | 95 | 5 | 1.5 | 60 |
| 1.3 | 0 | 100 | 1.5 | 60 |
| 1.5 | 0 | 100 | 1.5 | 60 |
| 1.6 | 95 | 5 | 1.5 | 60 |

HPLC traces and NMR spectra of the examples and some advanced intermediates are of increased complexity due to the fact that these compounds exist in an equilibrium of multiple rotameric forms. In the case of multiple peaks in the HPLC spectrum, the retention time of the main peak is reported.

Preparation of Intermediates

Synthesis of Acid Intermediates

| Acid | Name | Structure | Reference/Source |
|---|---|---|---|
| A-1 | 2-[1,2,3]Triazol-2-yl-benzoic acid | 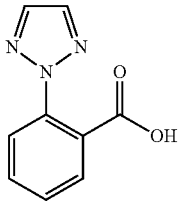 [SMILES: O=C(O)c1ccccc1-n1nccn1] | WO2008/143856, page 30, Compound B-1 |
| A-2 | 5-Methyl-2-[1,2,3]triazol-2-yl-benzoic acid | 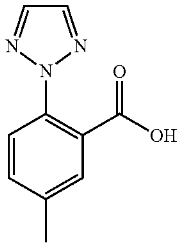 | WO2008/8518 page 31, compound A-3 |

-continued

| Acid | Name | Structure | Reference/Source |
|---|---|---|---|
| A-3 | 4-Methyl-2-[1,2,3]triazol-2-yl-benzoic acid | 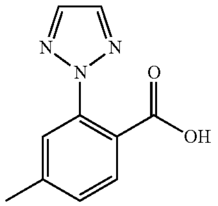 | WO2013/50938, Page 62, Intermediate B1.17 |
| A-4 | 3-Methyl-2-[1,2,3]triazol-2-yl-benzoic acid | 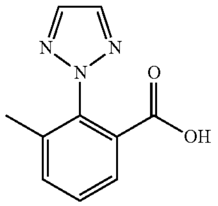 | WO2011/50200, Page 68-69, Intermediate 37 |
| A-5 | 4,5-Dimethyl-2-[1,2,3]triazol-2-yl-benzoic acid | 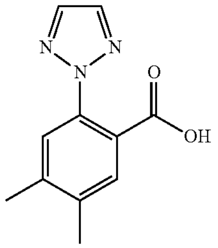 [SMILES: Cc1cc(C(=O)O)c(-n2nccn2)cc1C] | WO2013/50938, Page 61, Intermediate B1.14 |
| A-6 | 3,4-Dimethyl-2-[1,2,3]triazol-2-yl-benzoic acid | 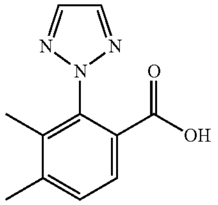 [SMILES: Cc1ccc(C(=O)O)c(-n2nccn2)c1C] | WO2013/68935, Page 58; Intermediate E-20 |
| A-7 | 3-Fluoro-2-[1,2,3]triazol-2-yl-benzoic acid | 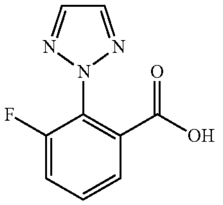 [SMILES: O=C(O)c1cccc(F)c1-n1nccn1] | WO2011/50198, Page 47, Intermediate 5 |
| A-8 | 4-Chloro-2-[1,2,3]triazol-2-yl-benzoic acid | 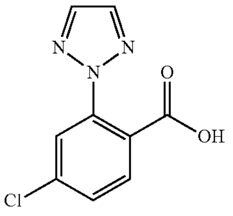 [SMILES: O=C(O)c1ccc(Cl)cc1-n1nccn1] | WO2011/50198, Page 47, Intermediate 6 |
| A-9 | 4-Fluoro-2-[1,2,3]triazol-2-yl-benzoic acid | 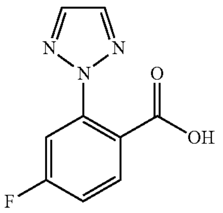 [SMILES: O=C(O)c1ccc(F)cc1-n1nccn1] | WO2011/50200, Page 54, Intermediate 16 |

-continued

| Acid | Name | Structure | Reference/Source |
|---|---|---|---|
| A-10 | 5-Fluoro-2-[1,2,3]triazol-2-yl-benzoic acid | 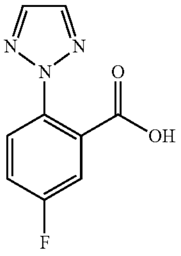 [SMILES: O=C(O)c1cc(F)ccc1-n1nccn1] | WO2011/50198, Page 45-46, Intermediate 1 |
| A-11 | 4,5-Difluoro-2-[1,2,3]triazol-2-yl-benzoic acid | 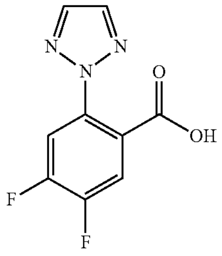 [SMILES: O=C(O)c1cc(F)c(F)cc1-n1nccn1] | WO2013/68935, Page 58; Intermediate E-24 |
| A-12 | 2-[1,2,3]Triazol-2-yl-5-trifluoromethyl-benzoic acid | 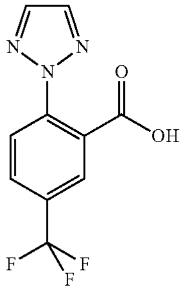 | WO2012/85852, Page 50, Intermediate 37 |
| A-13 | 5-Methoxy-2-[1,2,3]triazol-2-yl-benzoic acid | 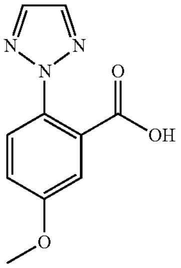 [SMILES: COc1ccc(-n2nccn2)c(C(=O)O)c1] | WO2011/50198, Page 49, Intermediate 10 |
| A-14 | 5-Methyl-2-pyrazol-1-yl-benzoic acid | 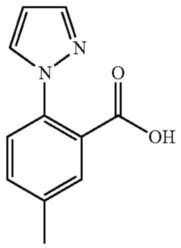 | WO2013/50938, Page 62, Intermediate B1.21 |
| A-15 | 5-Fluoro-2-pyrazol-1-yl-benzoic acid | 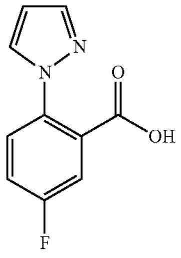 [SMILES: O=C(O)c1cc(F)ccc1-n1cccn1] | commercially available from Matrix Scientific: catalog number 053712, MDL number MFCD09054728 |

-continued

| Acid | Name | Structure | Reference/Source |
|---|---|---|---|
| A-16 | 2-(3-Methyl-[1,2,4]oxadiazol-5-yl)-benzoic acid | 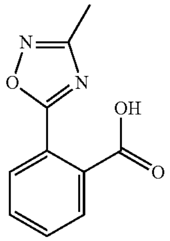 | commercially available from Apollo Scientific catalog number OR2076, MDL number: MFCD08741426 |
| A-17 | 2-[1,2,3]Triazol-2-yl-4-trifluoromethyl-benzoic acid | 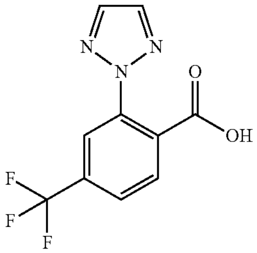 [SMILES: O=C(O)c1ccc(C(F)(F)F)cc1-n1nccn1] | WO2013/68935, Page 58; Intermediate E-21 |
| A-18 | 2-Pyrazol-1-yl-benzoic acid | 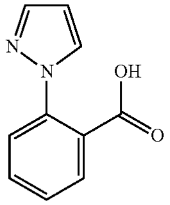 [SMILES: O=C(O)c1ccccc1-n1cccn1] | J. Am. Chem. Soc., 1958, 80, 6271 |
| A-19 | 2-Pyrrol-1-yl-benzoic acid | 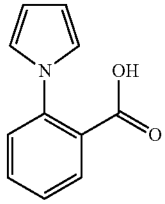 [SMILES: O=C(O)c1ccccc1-n1cccc1] | e.g. J. Chem. Soc., Perkin Trans. 1, 1980, 97; commercially available from Alfa Aesar reference L06069, registry number 10333-68-3 MDL number MFCD00051645 |
| A-20 | 4-Methoxy-2-[1,2,3]triazol-2-yl-benzoic acid | 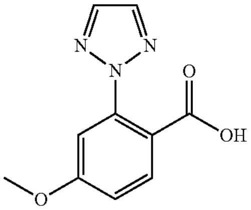 [SMILES: COc1ccc(C(=O)O)c(-n2nccn2)c1] | WO2011/50198, Page 73-74, Intermediate 73 |
| A-21 | 3-Fluoro-2-pyrimidin-2-yl-benzoic acid | 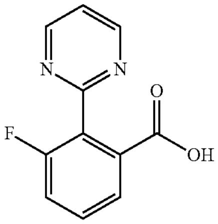 [SMILES: O=C(O)c1cccc(F)c1-c1ncccn1] | WO2011/50200, page 78, Intermediate 52 |

-continued

| Acid | Name | Structure | Reference/Source |
|---|---|---|---|
| A-23 | 2-Oxazol-2-yl-benzoic acid | 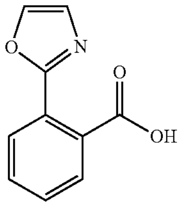 [SMILES: O=C(O)c1ccccc1-c1ncco1] | WO2006/76644, Page 212-213, Example 184 |
| A-24 | 5-Cyano-2-[1,2,3]triazol-2-yl-benzoic acid | 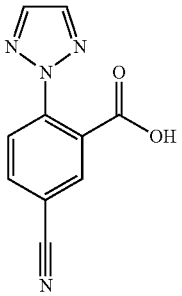 [SMILES: N#Cc1ccc(-n2nccn2)c(C(=O)O)c1] | WO2012/85852, Page 50, Intermediate 39 |
| A-25 | 2-(5-Methyl-[1,3,4]oxadiazol-2-yl)-benzoic acid | 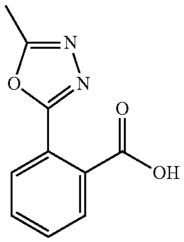 | commercially available from Enamine-BB catalog ID EN300-90215, MDL number MFCD09880459 |
| A-26 | 4-Fluoro-2-pyrimidin-2-yl-benzoic acid | 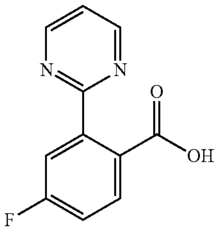 [SMILES: O=C(O)c1ccc(F)cc1-c1ncccn1] | WO2011/50200, page 95, intermediate 85 |
| A-27 | 2-Fluoro-6-[1,2,3]triazol-2-yl-benzoic acid | 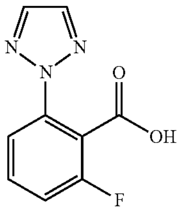 [SMILES: O=C(O)c1c(F)cccc1-n1nccn1] | WO2012/145581, intermediate 12, page 49-50 |
| A-34 | 3-Chloro-2-[1,2,3]triazol-2-yl-benzoic acid | 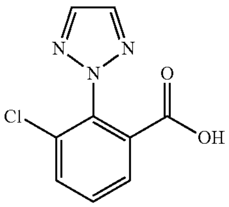 [SMILES: O=C(O)c1cccc(Cl)c1-n1nccn1] | WO2013/68935 E-23 in Table 6, p. 57 |

-continued

| Acid | Name | Structure | Reference/Source |
|---|---|---|---|
| A-35 | 2-Fluoro-3-methyl-6-[1,2,3]triazol-2-yl-benzoic acid | 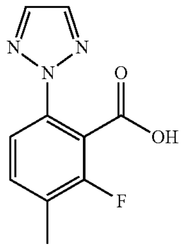 [SMILES: Cc1ccc(-n2nccn2)c(C(=O)O)c1F] | WO2012/85857 building block 34 p. 57-58 |

2-Pyrimidin-2-yl-benzoic acid A-22

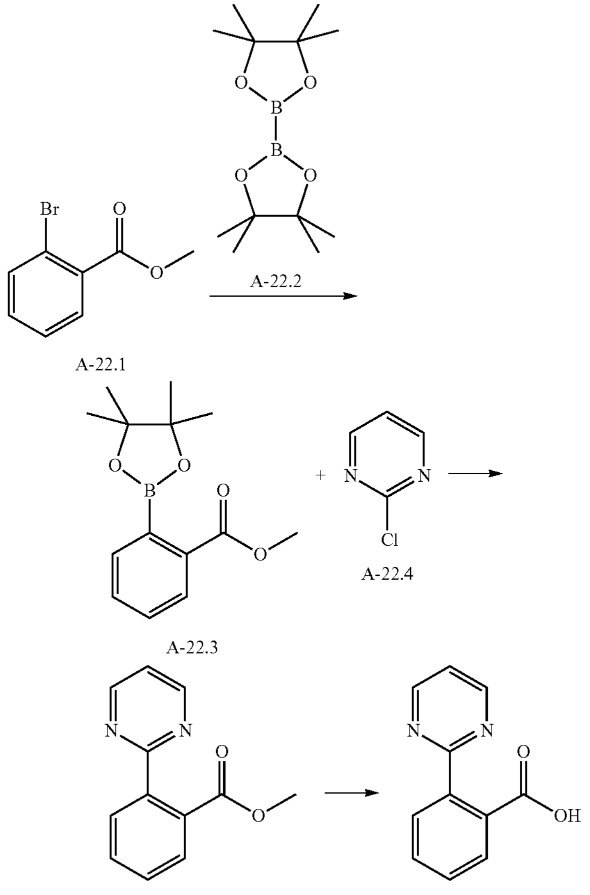

A-22.1 A-22.2 A-22.3 A-22.4 A-22.5 A-22

Step 1: A stirred mixture of A-22.1 (30.0 g, 140 mmol), A-22.2 (38.8 g, 154 mmol), Pd(dppf)$Cl_2$.DCM (11.4 g, 14.0 mmol) and potassium acetate (54.7 g, 558 mmol) in dioxane (300 mL) is heated at 100° C. for 2 h. After cooling the reaction is quenched with water and EA and the mixture filtered through a pad of celite. The phases are separated and the organic layer is dried, filtered and concentrated. The residue is purified by flash column chromatography (1-2% EA in hexane) to obtain A-22.3. ESI-MS: 263 [M+H]$^+$; HPLC (Rt): 2.54 min (method J)

Step 2: A stirred mixture of A-22.3 (25.0 g, 95.4 mmol), A-22.4 (12.0 g, 104.9 mmol), Pd(dppf)$Cl_2$.DCM (7.78 g, 9.54 mmol) and sodium carbonate (40.4 g, 381.5 mmol) in 2-methyl tetrahydrofuran (300 mL) and water (150 mL) is heated at 100° C. for 15 h. The reaction is cooled to RT and quenched with water and EA and filtered through a pad of celite. The layers are separated, the organic layer is dried, filtered and concentrated. The residue is purified by flash column chromatography on silica gel (EA/hexane=1:4) to provide 15.0 g of A-22.5. ESI-MS: 215 [M+H]$^+$; HPLC (Rt): 1.42 min (method K)

Step 3: A stirred mixture of A-22.5 (15.0 g, 70.0 mmol) and NaOH (4M aq. solution, 52.5 mL, 210 mmol) in 2-methyltetrahydrofuran (200 mL) is heated at 50° C. for 2 h. The organic solvent is distilled off, the aqueous layer acidified with conc. HCl and extracted with DCM. The combined organic phases are dried, filtered and concentrated. The residue is triturated with n-pentane yielding 5.8 g of A-22. ESI-MS: 201 [M+H]$^+$; HPLC (Rt): 1.39 min (method J)

3,5-Difluoro-2-[1,2,3]triazol-2-yl-benzoic acid A-28

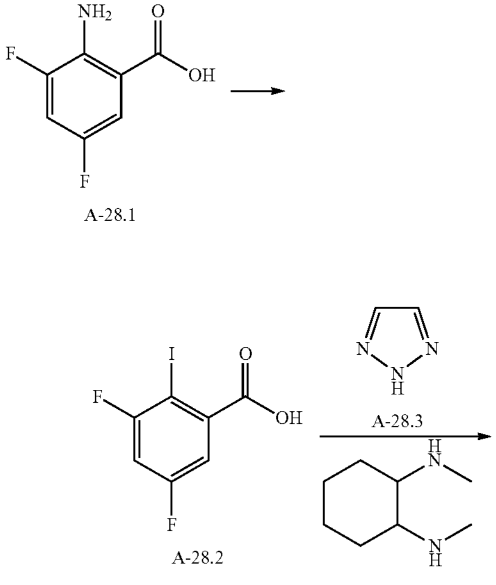

A-28.1 A-28.2 A-28.3 A-28.4

-continued

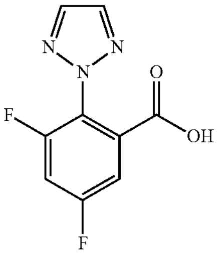

A-28

Step 1: A mixture of A-28.1 (9.80 g, 53.6 mmol) in water (70 mL) and $H_2SO_4$ (25 mL, 475 mmol) are cooled to 0° C. $NaNO_2$ (4.80 g, 69.0 mmol) in $H_2O$ (20 mL) is added dropwise and the reaction mixture is stirred for 1.5 h. To this mixture KI (44.5 g, 268 mmol) in $H_2O$ (40 mL) is added slowly. The reaction mixture is warmed to RT and then heated to 90° C. for 90 min. The mixture is allowed to cool to RT and $Na_2S_2O_3$ (aq. solution) is added until the color disappears. The precipitate is filtered and then dissolved in NaOH (4M aq. solution). The mixture is filtered, the filtrate is acidified with HCl (4M aq. solution) and the precipitate is filtered off, washed with water and dried to give 9.0 g of A-28.2. ESI-MS: 285 $[M+H]^+$; HPLC (Rt): 0.71 min (method C)

Step 2: A mixture of A-28.2, (3.50 g, 11.1 mmol), A-28.3 (1.56 g, 22.2 mmol), CuI (0.18 g, 0.89 mmol), A-28.4 (0.70 mL, 4.44 mmol) and $K_2CO_3$ (3.46 g, 23.9 mmol) in DMF (10 mL) is heated to 100° C. by microwave for 1.5 h. The mixture is poured into water and extracted with EA, the organic phase is washed with water. The combined aqueous phases are acidified with HCl (0.5M aq. solution) and extracted with EA. The organic phase is washed with brine, dried and concentrated to give the crude product which is purified by HPLC-MS (using a solvent gradient of $H_2O$+ 0.075% TFA with 5-35% ACN) to provide 1.25 g of A-28. ESI-MS: 226 $[M+H]^+$; HPLC (Rt): 1.88 min (method A)

4-Fluoro-2-(5-methyl-[1,3,4]oxadiazol-2-yl)-benzoic acid A-29

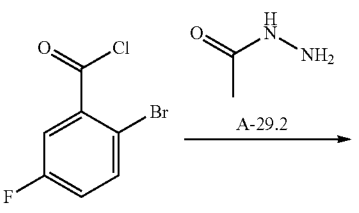

A-29.1

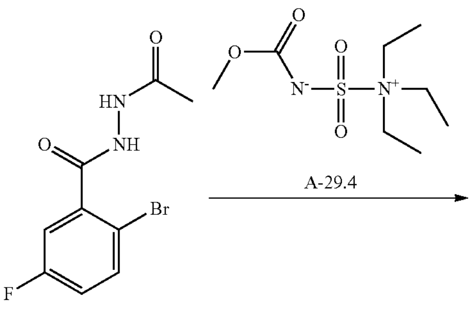

A-29.3

-continued

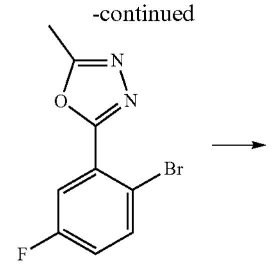

A-29.5

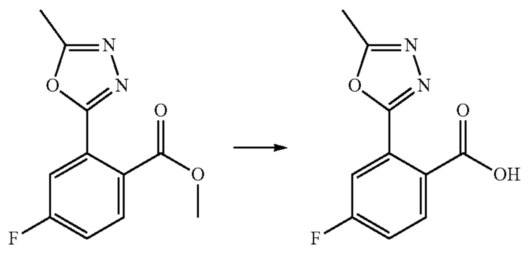

A-29.6 A-29

Step 1: To a mixture of A-29.1 (2.00 g, 8.40 mmol) in dry DCM (50 mL) is added A-29.2 (0.83 g, 10 mmol) and the reaction mixture is stirred at RT for 1 h. Another portion of A-29.2 (0.83 g, 10 mmol) is added and the reaction is stirred overnight. MeOH (5 mL) is added and the solvent is reduced to half the volume. The precipitate is filtered to provide 0.50 g of A-29.3. The filtrate is concentrated and purified by flash column chromatography on silica gel (using a solvent gradient from 100% DCM to 95% DCM and 5% MeOH) to provide another 1.1 g of A-29.3. ESI-MS: 275 $[M+H]^+$; HPLC (Rt): 0.47 min (method D)

Step 2: To a mixture of A-29.3 (1.60 g, 5.70 mmol) in DCM (50 mL) is added A-29.4 (2.70 g, 11.0 mmol) and the reaction is stirred overnight. $Na_2CO_3$ (2M aq. solution) is added, the organic phase is extracted with $Na_2CO_3$ (2M aq. solution), the combined organic phases are washed with brine, dried and concentrated to provide 0.80 g of A-29.5. ESI-MS: 257 $[M+H]^+$; HPLC (Rt): 0.47 min (method D)

Step 3: To a mixture of A-29.5 (0.80 g, 3.1 mmol) in dry MeOH (10 mL) and TEA (1.1 mL, 7.5 mmol) is added $Pd(dppf)Cl_2$.DCM (152 mg, 0.19 mmol). The reaction is stirred at 70° C. under a pressure of carbon monoxide (3 bar) for 4 h. The mixture is filtered, concentrated and purified by HPLC-MS (using a solvent gradient $H_2O$/ACN with $NH_4OH$) to provide 0.55 g of compound A29.6. ESI-MS: 237 $[M+H]^+$; HPLC (Rt): 0.88 min (method E)

Step 4: A mixture of A-29.6 (0.55 g, 2.3 mmol) in MeOH (4 mL) and NaOH (4M aq. solution, 2.9 mL, 12 mmol) is stirred at RT for 30 min. The mixture is concentrated and acidified with HCl (4M aq. solution) to pH2. The aqueous phase is extracted with EA, dried and concentrated to provide 0.42 g of compound A-29. ESI-MS: 223 $[M+H]^+$; HPLC (Rt): 0.10 min (method D)

The following examples are prepared in analogy to the above described procedure using the corresponding starting material:

| Intermediate | Name | Structure | ESI-MS [M + H]+ | HPLC (Rt) [min] | HPLC method |
|---|---|---|---|---|---|
| A-30 | 3-Fluoro-2-(5-methyl-[1,3,4]oxadiazol-2-yl)-benzoic acid | 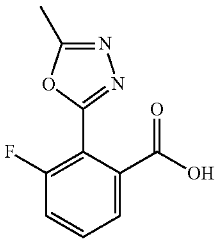 [SMILES: Cc1nnc(-c2c(F)cccc2C(=O)O)o1] | 223 | 0.10 | D |
| A-31 | 4-Methyl-2-(5-methyl-[1,3,4]oxadiazol-2-yl)-benzoic acid | 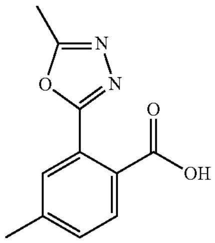 [SMILES: Cc1ccc(C(=O)O)c(-c2nnc(C)o2)c1] | 271 | 0.22 | D |
| A-32 | 3-Methyl-2-(5-methyl-[1,3,4]oxadiazol-2-yl)-benzoic acid | 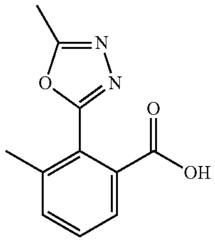 [SMILES: Cc1nnc(-c2c(C)cccc2C(=O)O)o1] | 219 | 0.10 | D |

2-(2-Methyl-oxazol-5-yl)-benzoic acid A-33

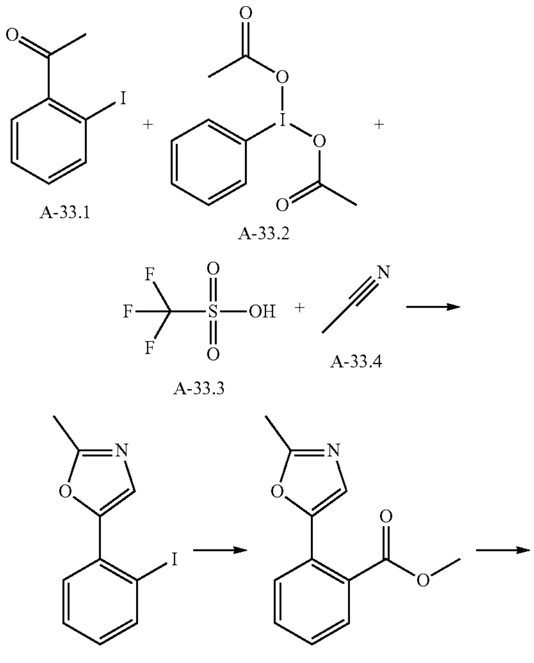

A-33.1 A-33.2 A-33.3 A-33.4 A-33.5 A-33.6

-continued

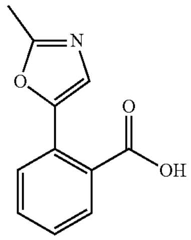

A-33

Step 1: To a mixture of A-33.2 (17.00 g, 538 mmol) in DCM (250 mL) is added A-33.3 (16.00 g, 106 mmol) and the mixture is stirred for 1 h. Then A-33.1 (6.5 g, 26 mmol) and A-33.4 (11 g, 264 mmol) are added and the reaction is stirred at 45° C. for 5 h. The pH of the reaction mixture is adjusted to pH8 with $NaHCO_3$ (sat. aq. solution), and the mixture is extracted with DCM and the combined organic layers are dried and concentrated. The residue is purified by flash column chromatography on silica gel (using a solvent gradient of petroleum ether: EA from 40:1 to 20:1) to provide 2.20 g of A-33.5. ESI-MS: 286 $[M+H]^+$; HPLC (Rt): 1.55 (method S)

Step 2: A mixture of A-33.5 (2.20 g, 7.89 mmol), TEA (4.00 g, 40.0 mmol) Pd(dppf)$Cl_2$.DCM (0.58 g, 0.79 mmol) in MeOH (70 mL) is stirred at 50° C. and under an atmosphere of carbon monoxide (50 psi) for 16 h. The mixture is concentrated and purified by flash column chromatography on silica gel (using a solvent gradient of petroleum ether: EA from 80:1 to 40:1) to provide 2.0 g of A-33.6. ESI-MS: 218 $[M+H]^+$; HPLC (Rt): 0.71 min (method C)

Step 3: A mixture of A-33.6 (2.00 g, 9.20 mmol), MeOH (10 mL) and LiOH monohydrate (0.46 g, 11 mmol) is stirred at 25° C. for 16 h. The organic solvent is evaporated, the residue is acidified with HCl (1M aq. solution) to pH3-4. The precipitate is filtered and dried to provide 1.4 g of A-33. ESI-MS: 204 [M+H]$^+$; HPLC (Rt): 2.38 min (method R)

3,4-Difluoro-2-[1,2,3]triazol-2-yl-benzoic acid A-36

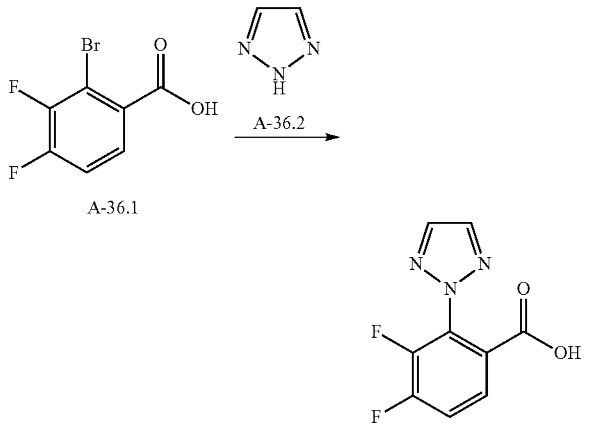

A-36.1 A-36.2 A-36

A mixture of A-36.1 (9.0 g, 36 mmol), A-36.2 (5.3 g, 72 mmol), CuI (0.70 g, 3.6 mmol) and $K_2CO_3$ (11 g, 78 mmol) in DMF (100 mL) is heated to 120° C. for 16 h. The mixture is acidified with HCl (0.5M aq. solution) to pH2. The mixture is extracted with EA, the organic phase is washed with brine, dried and concentrated to give the crude product which is purified by HPLC-MS (using a solvent gradient $H_2O$+0.075% TFA with 5-35% ACN) to provide 3.0 g of A-36. ESI-MS: 248 [M+Na]$^+$; HPLC (Rt): 0.45 min (method B)

2-(5-Methyl-[1,2,4]oxadiazol-3-yl)-benzoic acid A-37

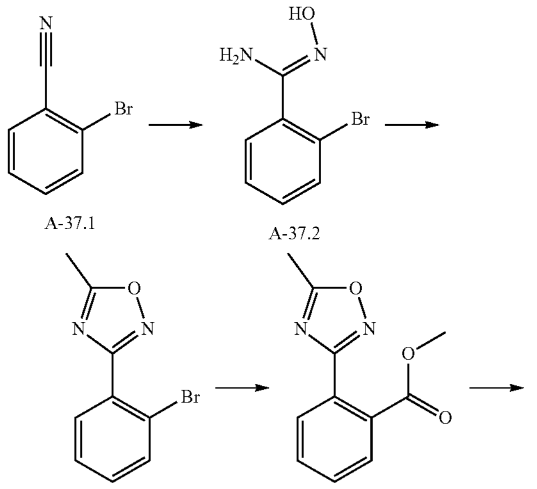

A-37.1 A-37.2 A-37.3 A-37.4

-continued

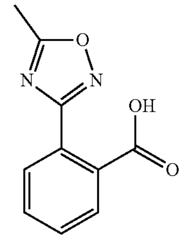

A-37

Step 1: A mixture of $NH_2OH.HCl$ (29 g, 0.41 mol) and $K_2CO_3$ (57 g, 0.41 mol) in EtOH (500 mL) is stirred at 25° C. for 30 min. A-37.1 (30 g, 0.17 mol) is added and the reaction mixture is heated to 70° C. for 12 h. After filtration, the solvent is evaporated and the residue purified by flash column chromatography on silica gel (petroleum ether/EA=5:1 to 2:1) to obtain 25 g of A-37.2.

Step 2: To a mixture of A-37.2 (18.0 g, 0.084 mol) in ACN (200 mL) is added acetic anhydride (10.0 g; 0.10 mol) and TEA (17.0 g, 0.17 mol). The mixture is stirred at 120° C. for 48 h. The mixture is concentrated in vacuum and the residue purified by flash column chromatography on silica gel (petroleum ether/EA=1/0 to 10/1) to afford 9.0 g of A-37.3. ESI-MS: 239/241 [M+H]$^+$; HPLC (Rt): 1.43 min (method S)

Step 3: To a mixture of A-37.3 (9 g, 0.038 mol) and TEA (11.5 g; 0.114 mol) in MeOH (200 mL) is added Pd(dppf)$Cl_2$.DCM (1.0 g, 1.2 mmol). The mixture is stirred at 50° C. under an atmosphere of carbon monoxide (50 psi) for 16 h. The mixture is concentrated and the residue purified by flash column chromatography on silica gel (petroleum ether/EA=1/0 to 5/1) to afford 4.0 g of A-37.4. ESI-MS: 219 [M+H]$^+$; HPLC (Rt): 1.28 min (method S)

Step 4: To a mixture of A-37.4 (4.0 g, 0.018 mol) in MeOH (40 mL) and $H_2O$ (4 mL) is added NaOH (1.5 g, 0.037 mol) at 25° C. under nitrogen. The mixture is stirred at 70° C. for 4 h. The mixture is concentrated. The residue is dissolved in $H_2O$, acidified with HCl (4M aq. solution) to pH3 and filtered to obtain 2.2 g of A-37. ESI-MS: 205 [M+H]$^+$; HPLC (Rt): 2.13 min (method T)

2-(1-Methyl-1H-pyrazol-4-yl)-benzoic acid A-38

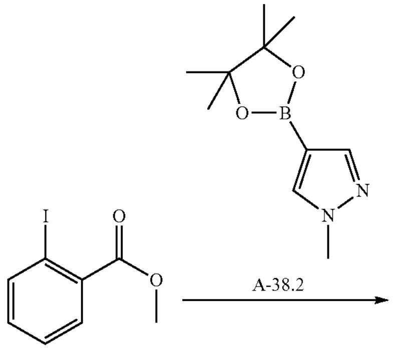

A-38.2 A-38.1

-continued

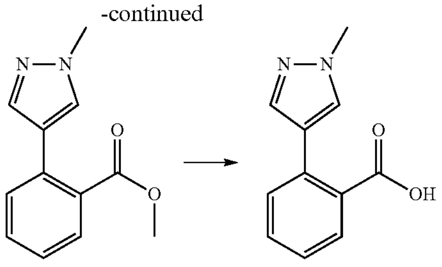

A-38.3 A-38

Step 1: A mixture of A-38.1 (2.0 g, 7.6 mmol), A-38.2 (1.8 g, 8.4 mmol), $K_2CO_3$ (1.6 g, 15 mmol), 1c) Pd(dppf) $Cl_2$.DCM (0.28 g, 0.38 mmol) in dioxane (6 mL) and water (3 mL) is heated at 140° C. by microwave for 15 min and then for 25 h at 160° C. The mixture is filtered and concentrated. The crude mixture is purified by HPLC-MS (using a solvent gradient $H_2O$/ACN with $NH_4OH$) to provide 1.32 g of compound 3. ESI-MS: 217 $[M+H]^+$; HPLC (Rt): 0.49 min (method U)

Step 2: A mixture of 1.3 g (6.1 mmol) A-38.3, NaOH (4M aq. solution, 7.5 mL, 30 mmol) in MeOH (7.5 mL) is stirred at RT overnight. The mixture is concentrated, water is added and extracted with DCM/EA. The organic phases are dried and concentrated to provide 750 mg of A-38. ESI-MS: 203 $[M+H]^+$; HPLC (Rt): 0.40 min (method U)

Synthesis of Amine Intermediates

Ethyl-[(S)-1-methyl-2-(5-trifluoromethyl-pyrimidin-2-yloxy)-ethyl]-amine hydrochloride B-1

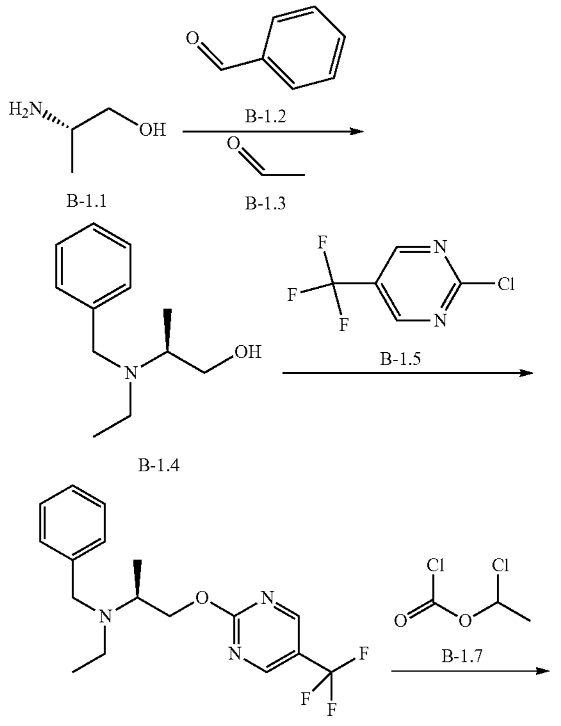

B-1.6

-continued

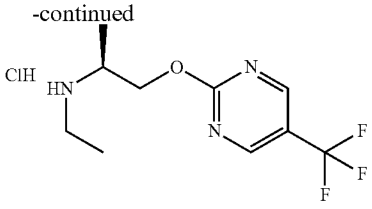

B-1

Step 1: A mixture of B-1.1 (5.0 g, 67 mmol) and B-1.2 (6.8 mL, 67 mmol) in 180 mL of THF is stirred at RT for 1 h. Sodium triacetoxyborohydride (45 g, 200 mmol) is added at 0° C. and the reaction mixture is stirred at RT for 30 min. B-1.3 (11.2 mL, 200 mmol) in 20 mL of THF is added dropwise within 10 min at 0° C. and the mixture is stirred at RT overnight. Another portion of B-1.3 (10 mL, 179 mmol) is added and the reaction mixture stirred at RT for 3 h. The precipitate is filtered and washed with THF and DCM. 200 mL of $NaHCO_3$ (sat. aq. solution) and solid $NaHCO_3$ is added to the filtrate until gas formation stopped. The aqueous phase is extracted with DCM, the organic phase is dried and concentrated to provide 11.8 g of B-1.4. ESI-MS: 194 $[M+H]^+$; HPLC (Rt): 1.13 min (method E)

Step 2: To a mixture of B-1.4 (3.5 g, 18 mmol) in dry dioxane (60 mL) under nitrogen is added portion wise potassium tert-butoxide (4.5 g, 40 mmol) and the mixture is stirred for 15 min before B-1.5 (3.6 g, 20 mmol) is added. The mixture is heated to 60° C. for 3 h, stirred overnight at RT and concentrated. Water is added and the aq. phase extracted with EA. The organic phase is dried and concentrated. The crude product is purified by silica column (using a solvent gradient from 100% cyclohexane to 85% cyclohexane and 15% EA) to provide 1.30 g of B-1.6. ESI-MS: 340 $[M+H]^+$; HPLC (Rt): 1.47 min (method M)

Step 3: To a mixture of B-1.6 (1.3 g, 3.5 mmol) in dry 1,2-dichloroethane (15 mL) at 0° C. under nitrogen is added B-1.7 (0.45 mL, 4.1 mmol). The mixture is heated to reflux and stirred for 4 h. MeOH (15 mL) is added and the reaction is heated to 60° C. and stirred for 1 h. The solvent is evaporated and the crude mixture is purified by flash column chromatography on silica gel (using a solvent gradient from 100% DCM to 94% DCM and 6% MeOH+0.6% $NH_3$). The obtained compound is taken up into EA and 1.7 mL of HCl (2M aq. solution) is added under stirring. The solvent is removed and the residue obtained is triturated with $Et_2O$ and filtered to give 0.43 g of B-1. ESI-MS: 250 $[M+H]^+$; HPLC (Rt): 3.17 min (method N), $^1H$ NMR (400 MHz, DMSO-d6) δ ppm 1.23 (t, J=7.24 Hz, 3H) 1.36 (d, J=7.04 Hz, 3H) 3.05 (dd, J=7.04, 3.91 Hz, 2H) 3.62-3.72 (m, 1H) 4.52-4.71 (m, 2H) 9.03 (br. s., 2H) 9.12 (d, J=0.78 Hz, 2H)

(S)-2-(tert-Butyl-dimethyl-silanyloxy)-1-methyl-ethylamine B-2

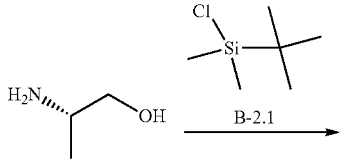

B-1.1

-continued

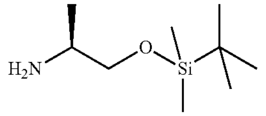

B-2

To a stirred mixture of B-1.1 (2.00 g, 26.6 mmol) and B-2.1 (4.01 g, 26.6 mmol) in dry DCM (15 mL) a solution of TEA (5.39 g, 53.3 mmol) in dry DCM (15 mL) is added dropwise. The mixture is stirred at RT overnight. $NH_4Cl$ (sat. aq. solution) is added and the aqueous phase is extracted with DCM, dried and concentrated to provide 4.7 g of B-2. ESI-MS: 190 $[M+H]^+$; HPLC (Rt): 0.88 min (method M), $^1H$ NMR (500 MHz, DMSO-d6) δ ppm 0.03 (s, 6H), 0.87 (s, 9H), 0.91 (d, J=6.36 Hz, 3H), 2.31 (s (broad), 2H), 2.79 (m, 1H), 3.27-3.35 (m, 2H)

Synthesis of Alcohol Intermediates (S)-2-Ethylamin-propan-1-ol hydrochloride C-1

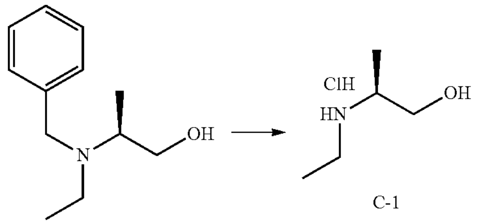

B-1.4

C-1

To a mixture of B-1.4 (9.01 g, 46.6 mmol) in MeOH (200 mL) is added Pd/C (0.90 g). The reaction is stirred at RT and under a pressure of hydrogen (4 bar) for 4 h. The catalyst is filtered off, HCl (4M in dioxane, 14.0 mL, 56.0 mmol) is added and the mixture is concentrated to provide 6.00 g of C-1. ESI-MS: 104 $[M+H]^+$; HPLC (Rt): 0.20 min (method L), $^1H$ NMR (500 MHz, DMSO-d6) δ ppm 1.17-1.22 (m, 3H), 2.94 (dqd, 2H), 3.11-3.20 (m, 1H), 3.51 (dd, 1H), 3.62 (dd, 1H).

N-Ethyl-3-fluoro-N—((S)-2-hydroxy-1-methyl-ethyl)-2-[1,2,3]triazol-2-yl-benzamide C-2

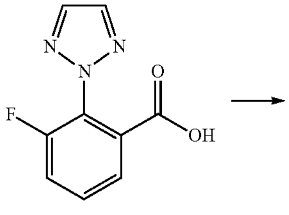

A-7

-continued

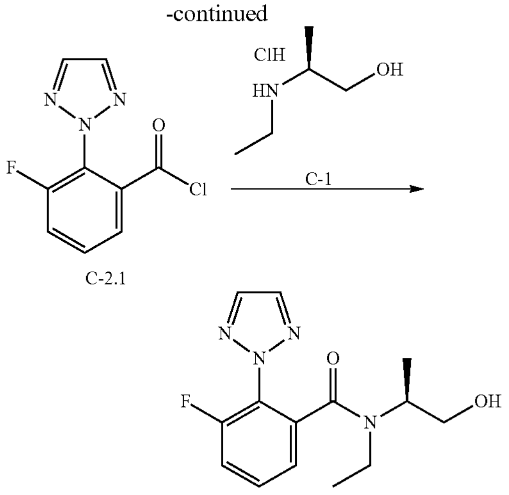

C-2.1

C-2

Step 1: A mixture of A-7 (1.24 g, 5.99 mmol), thionyl chloride (9.00 mL, 123 mmol) in DMF (0.25 mL) and DCM (7.0 mL) is stirred at RT for 1 h. The mixture is concentrated and concentrated to provide 1.68 g of C-2.1. ESI-MS: 222 $[M+H]^+$; HPLC (Rt): 0.53 min (method H)

Step 2: To a mixture of C-2.1 (1.68 g, 5.96 mmol), TEA (2.09 mL, 14.9 mmol), THF (50 mL) and DCM (20 mL) is added C-1 (0.92 g, 6.55 mmol). The mixture is stirred at RT overnight. The precipitate is filtered off, washed with EA and the filtrate is concentrated. The crude mixture is purified by HPLC-MS (using a solvent gradient $H_2O$/ACN with $NH_4OH$) to provide 1.33 g of C-2. ESI-MS: 291 $[M+H]^+$; HPLC (Rt): 0.46 min (method H)

N-Ethyl-N—((S)-2-hydroxy-1-methyl-ethyl)-2-[1,2,3]triazol-2-yl-benzamide C-3

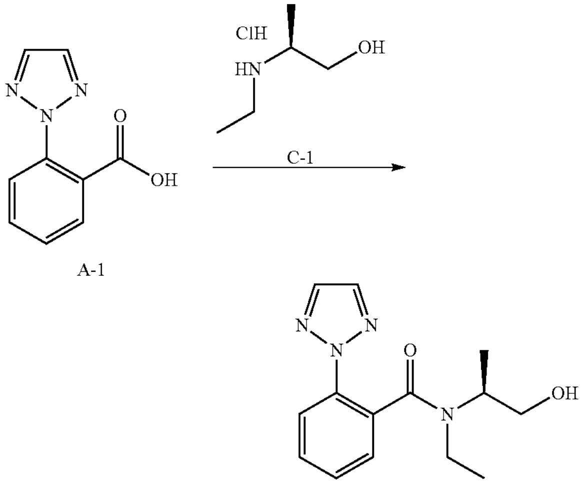

A-1

C-3

A mixture of A-1 (0.72 g, 3.8 mmol) and thionyl chloride (0.36 mL, 5.0 mmol) in toluene (7 mL) and a drop of DMF is heated to 60° C. for 2 h, then cooled and concentrated. The residue is dissolved in 5 mL of dry DCM and added dropwise to a stirred mixture of C-1 (0.65 g, 4.64 mmol) and TEA (1.44 mL, 10.3 mmol) in dry DCM (10 mL) at 0° C.

The reaction is stirred at RT for 2 h. Water is added and the organic layer is separated, washed with citric acid (10% aq. solution) and with $NaHCO_3$ (sat. aq. solution). The organic layer is dried and concentrated to provide 0.94 g of C-3. ESI-MS: 275.1 [M+H]$^+$, HPLC (Rt): 0.69 min (method M)

N-Ethyl-N—((S)-2-hydroxy-1-methyl-ethyl)-4-methoxy-2-[1,2,3]triazol-2-yl-benzamide C-4

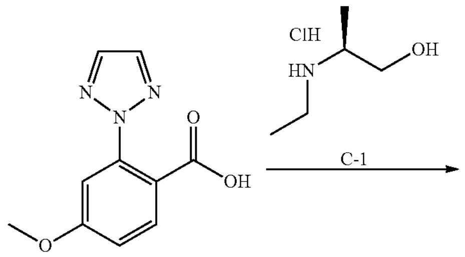

A-20

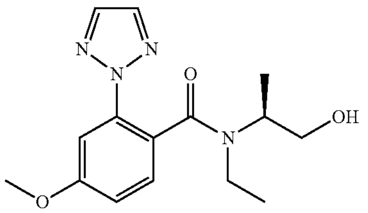

C-4

To a mixture of A-20 (314 mg, 1.43 mmol), C-1 (200 mg, 1.43 mmol) and HATU (0.60 g, 1.58 mmol) in dry DMF (5.0 mL) is added DIPEA (0.75 mL, 4.3 mmol) and the reaction is stirred at RT overnight. The reaction mixture is concentrated and the residue dissolved in EA, the mixture is washed with citric acid (10% aq. solution) and the organic phase is concentrated. The crude product is purified by silica column (using a solvent gradient from 100% DCM to 95% DCM and 5% MeOH) to provide 280 mg of C-4. ESI-MS: 305.2 [M+H]$^+$; HPLC (Rt): 0.77 min (method M)

N-Ethyl-4-fluoro-N—((S)-2-hydroxy-1-methyl-ethyl)-2-pyrimidin-2-yl-benzamide C-5

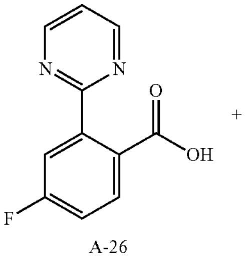

A-26

-continued

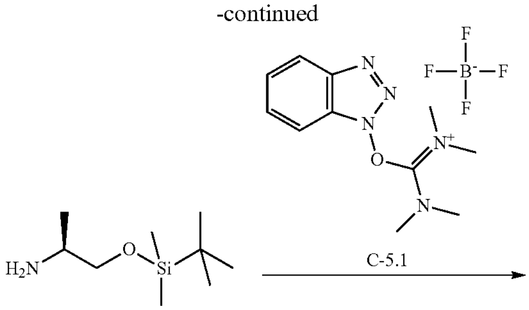

B-2

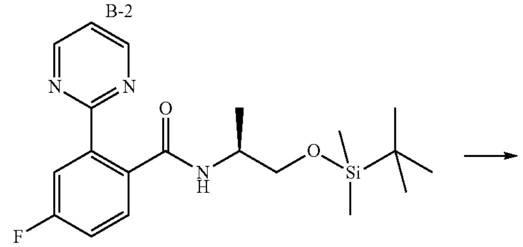

C-5.2

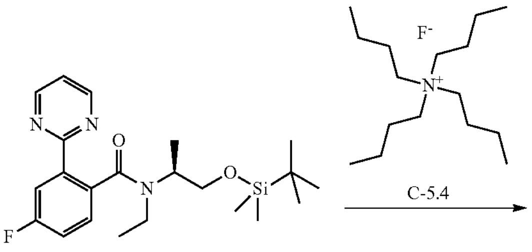

C-5.3

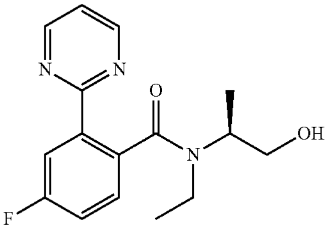

C-5

Step 1: A mixture of A-26 (0.20 g, 0.92 mmol), DIPEA (0.31 mL, 1.0 mmol) and C-5.1 (0.32 g, 1.0 mmol) in dry DMF (4.0 mL) is stirred under nitrogen for 30 min. B-2 (0.19 g, 1.0 mmol) is added and the reaction mixture is stirred for 2 h at RT. The crude mixture is poured into water and extracted with EA. The organic phase is dried and concentrated. The residue is purified by flash column chromatography on silica gel (using a solvent gradient from 100% cyclohexane to 40% cyclohexane and 60% EA) to provide 0.22 g of C-5.2. ESI-MS: 389, [M+H]$^+$; HPLC (Rt): 1.38 min (method M)

Step 2: Under nitrogen, a mixture of C-5.2 (0.12 g, 0.31 mmol) and ethyl iodide (96 mg, 0.62 mmol) in dry DMF (2.5 mL) is stirred at 0° C. Potassium tert-butoxide (52 mg, 0.46 mmol) is added and the reaction is stirred at 0° C. for 1 h. Water is added and the crude mixture is extracted with EA. The organic phase is dried and concentrated. The residue is purified by flash column chromatography on silica gel (using a solvent gradient from 100% cyclohexane to 50% cyclohexane and 50% EA) to provide 140 mg (purity 90%) of C-5.3. ESI-MS: 418 [M+H]$^+$; HPLC (Rt): 1.60 min (method M)

Step 3: To a stirred mixture of C-5.3 (140 mg, 0.30 mmol, purity 90%) in dry THF (3.0 mL) at 0° C. is added C-5.4 (595 mg, 0.67 mmol). The reaction is stirred at 0° C. for 1 h and is then concentrated. The residue is purified by flash column chromatography on silica gel (using a solvent gradient from 100% DCM to 90% DCM and 10% MeOH) to provide 80 mg of C-5. ESI-MS: 304 $[M+H]^+$; HPLC (Rt): 0.75 min (method M)

Preparation of Compounds of the Present Invention

Example 1

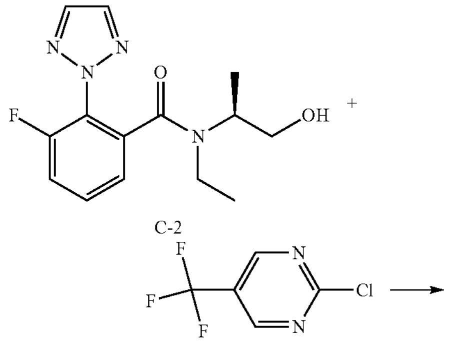

C-2

1.1

-continued

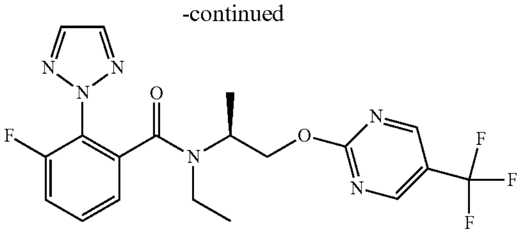

Example 1

To a mixture of C-2 (40 mg, 0.14 mmol) in dry DMF (2 mL) is added NaH (60% in mineral oil, 7.0 mg, 0.17 mmol) and the mixture is stirred at RT for 1 h. 1.1 (60 mg, 0.33 mmol) is added and the mixture is stirred for 4 h, then diluted with MeOH, filtered and the crude product is purified by HPLC-MS (using a solvent gradient $H_2O$/ACN with TFA) to provide 14 mg of Example 1. ESI-MS: 439 $[M+H]^+$; HPLC (Rt): 1.14 min (method E)

The following examples are prepared in analogy to the above described procedure: For the synthesis of Examples 24 and 30 the work-up is done as follows: The reaction mixture is diluted with water and extracted with EA. The organic phase is dried and concentrated and then purified by HPLC-MS or flash column chromatography on silica gel.

| Example | Structure | ESI-MS $[M + H]^+$ | HPLC (Rt) [min] | HPLC method |
|---|---|---|---|---|
| 24 | 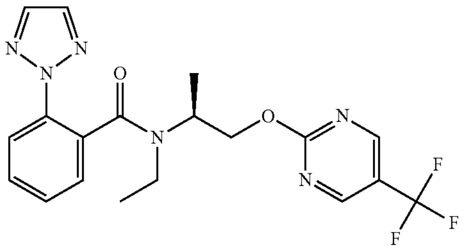 [SMILES: CCN(C(=O)c1ccccc1-n1nccn1)[C@@H](C)COc1ncc(C(F)(F)F)cn1] | 423 $(M + Na)^+$ | 4.37 | Q |
| 30 | 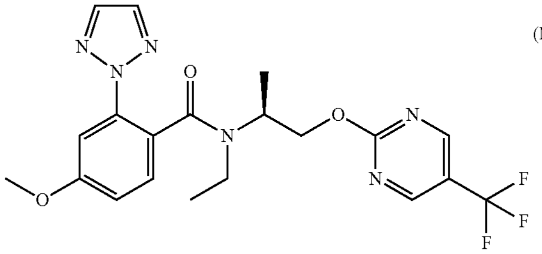 | 473 $(M + Na)^+$ | 3.54 | N |
| 32 | 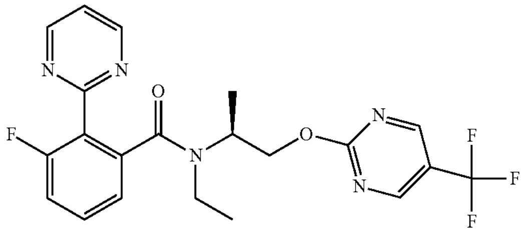 [SMILES: CCN(C(=O)c1cccc(F)c1-c1ncccn1)[C@@H](C)COc1ncc(C(F)(F)F)cn1] | 472 $(M + Na)^+$ | 3.29 | N |

Example 2

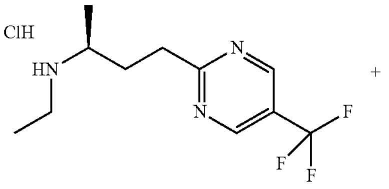

B-1

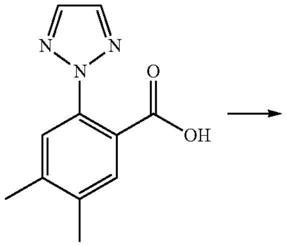

A-5

-continued

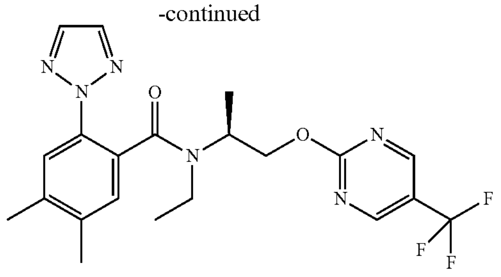

Example 2

To a mixture of A-5 (2.2 mg, 0.010 mmol) in ACN (0.10 mL) is added a mixture of B-1 (2.86 mg, 0.010 mmol) and DIPEA (5.19 μl, 0.030 mmol) in ACN (0.10 mL). Then CIP (3.62 mg, 0.010 mmol) in ACN (0.10 mL) is added and the reaction mixture is shaken at RT for 4 h. DMF (100 μL) and $K_2CO_3$ (3M aq. solution, 15 μL) is added and the mixture is shaken for 1 h. The mixture is then filtered through a pad of basic aluminium oxide, washed with DMF/MeOH (9/1) and concentrated to provide 4.8 mg of Example 2. ESI-MS: 449 $[M+H]^+$; HPLC (Rt): 0.93 min (method P)

The following examples are prepared in analogy to the above described procedure using the corresponding acid (see Acid Intermediates) and amine (see Amine Intermediates) as described before.

| Example | Structure | ESI-MS $[M + H]^+$ | HPLC (Rt) [min] | HPLC method |
|---|---|---|---|---|
| 5 | 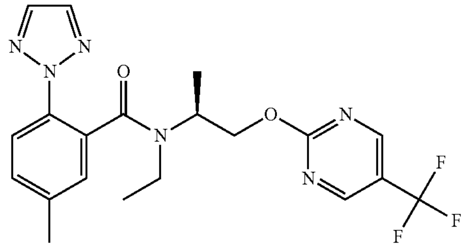 [SMILES: CCN(C(=O)c1cc(C)ccc1-n1nccn1)[C@@H](C)COc1ncc(C(F)(F)F)cn1] | 435 | 0.88 | P |
| 7 | 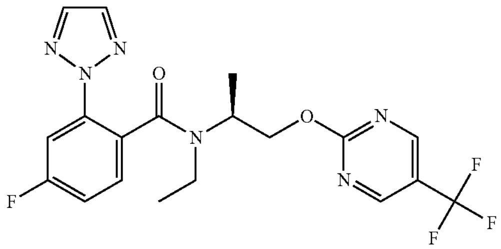 [SMILES: CCN(C(=O)c1ccc(F)cc1-n1nccn1)[C@@H](C)COc1ncc(C(F)(F)F)cn1] | 439 | 0.86 | P |
| 8 | 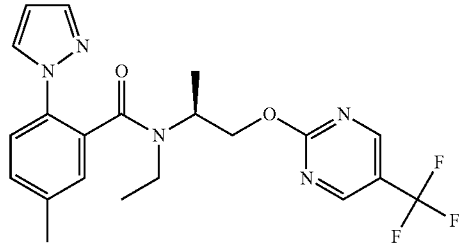 [SMILES: CCN(C(=O)c1cc(C)ccc1-n1cccn1)[C@@H](C)COc1ncc(C(F)(F)F)cn1] | 434 | 0.87 | P |

-continued
| | | | | |
|---|---|---|---|---|
| 10 | 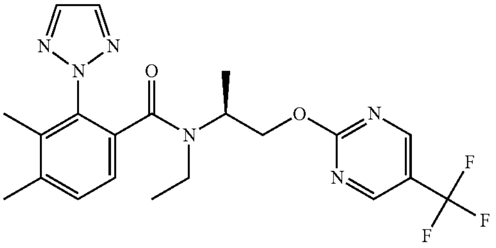 [SMILES: CCN(C(=O)c1ccc(C)c(C)c1-n1nccn1)[C@@H](C)COc1ncc(C(F)(F)F)cn1] | 449 | 0.90 | P |
| 11 | 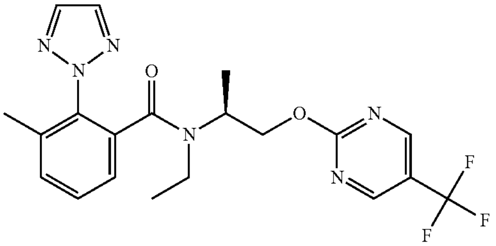 [SMILES: CCN(C(=O)c1cccc(C)c1-n1nccn1)[C@@H](C)COc1ncc(C(F)(F)F)cn1] | 435 | 0.87 | P |
| 15 | 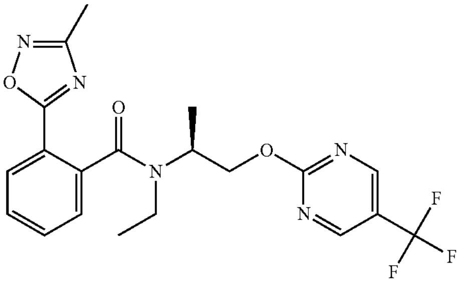 [SMILES: CCN(C(=O)c1ccccc1-c1nc(C)no1)[C@@H](C)COc1ncc(C(F)(F)F)cn1] | 436 | 0.84 | P |
| 18 | 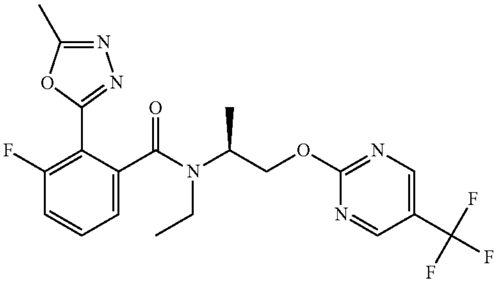 [SMILES: CCN(C(=O)c1cccc(F)c1-c1nnc(C)o1)[C@@H](C)COc1ncc(C(F)(F)F)cn1] | 454 | 0.76 | P |
| 19 | 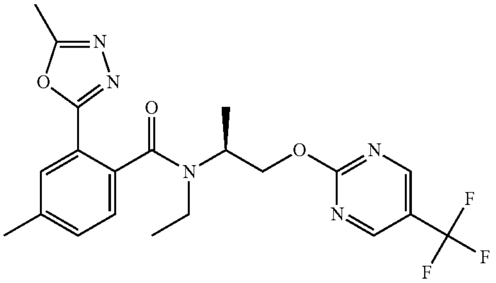 [SMILES: CCN(C(=O)c1ccc(C)cc1-c1nnc(C)o1)[C@@H](C)COc1ncc(C(F)(F)F)cn1] | 450 | 0.80 | P |
| 20 | 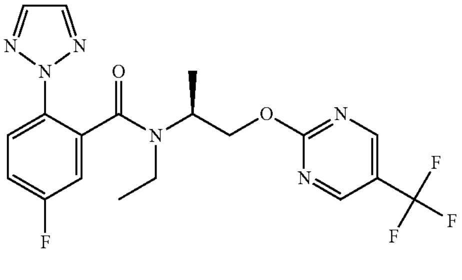 [SMILES: CCN(C(=O)c1cc(F)ccc1-n1nccn1)[C@@H](C)COc1ncc(C(F)(F)F)cn1] | 439 | 0.85 | P |

-continued
| | | | | |
|---|---|---|---|---|
| 21 | 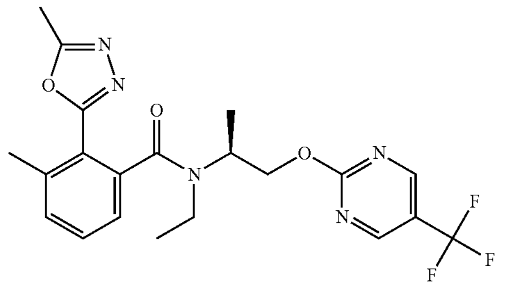 [SMILES: CCN(C(=O)c1cccc(C)c1-c1nnc(C)o1)[C@@H](C)COc1ncc(C(F)(F)F)cn1] | 450 | 0.79 | P |
| 22 | 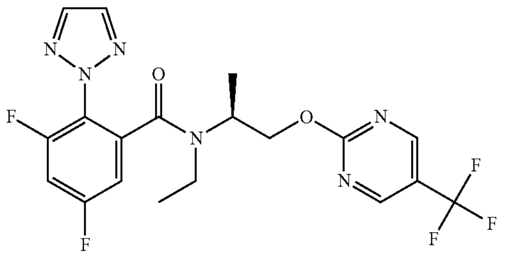 [SMILES: CCN(C(=O)c1cc(F)cc(F)c1-n1nccn1)[C@@H](C)COc1ncc(C(F)(F)F)cn1] | 457 | 0.86 | P |
| 34 | 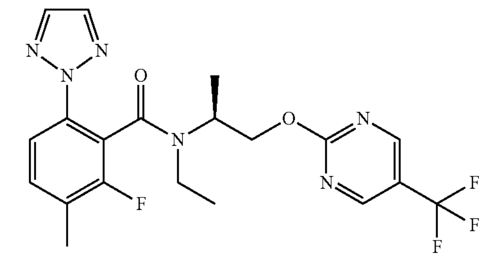 [SMILES: CCN(C(=O)c1c(-n2nccn2)ccc(C)c1F)[C@@H](C)COc1ncc(C(F)(F)F)cn1] | 475.2 [M + Na]+ | 1.00 | V |
| 35 | 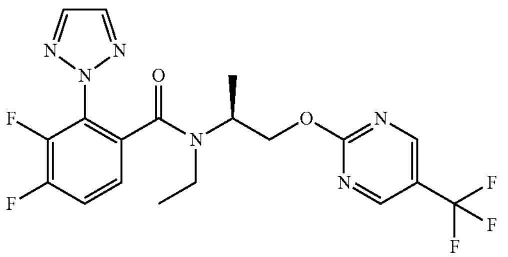 [SMILES: CCN(C(=O)c1ccc(F)c(F)c1-n1nccn1)[C@@H](C)COc1ncc(C(F)(F)F)cn1] | 479.2 [M + Na]+ | 0.93 | V |
| 36 | 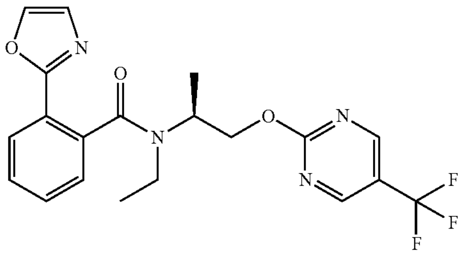 [SMILES: CCN(C(=O)c1ccccc1-c1ncco1)[C@@H](C)COc1ncc(C(F)(F)F)cn1] | 443.2 [M + Na]+ | 0.86 | V |

-continued

| Example | Structure | ESI pos. (Loop-Inj.) | HPLC (Rt) [min] | HPLC method |
|---|---|---|---|---|
| 13 | 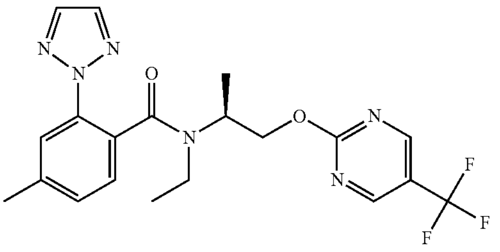 [SMILES: CCN(C(=O)c1ccc(C)cc1-n1nccn1)[C@@H](C)COc1ncc(C(F)(F)F)cn1] | 435 | 1.08 | F |
| 14 | 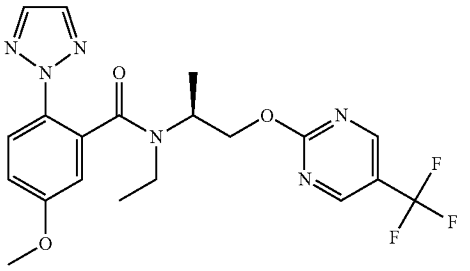 [SMILES: CCN(C(=O)c1cc(OC)ccc1-n1nccn1)[C@@H](C)COc1ncc(C(F)(F)F)cn1] | 451 | 1.06 | F |

Example 31

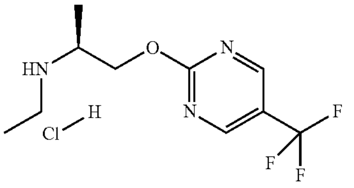

B-4

+

-continued

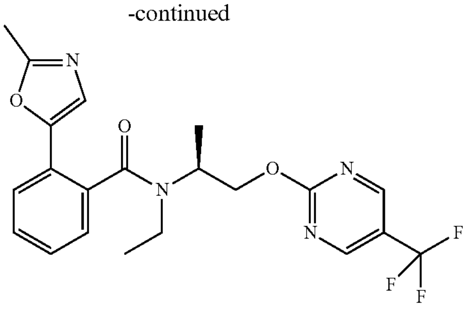

Example 31

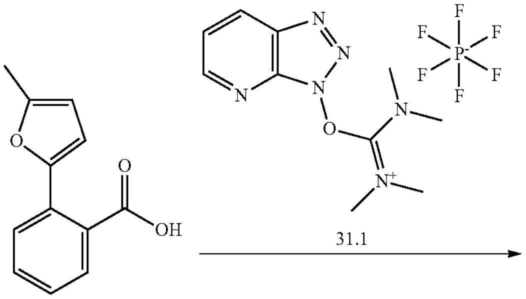

A-33

To a mixture of A-33 (43 mg, 0.21 mmol) in dry DMF (4.0 mL) 31.1 (120 mg, 0.32 mmol) and DIPEA (182 μL, 1.05 mmol) is added. After 10 min B-4 (60 mg, 0.21 mmol) is added and the mixture is stirred at RT for 4 h. The mixture is treated with water, washed with $NH_4Cl$ (aq. solution), dried and concentrated. The crude mixture is purified by HPLC-MS (using a solvent gradient $H_2O$/ACN with $NH_4COOH$) to provide 35 mg of Example 31. ESI-MS: 435 $[M+H]^+$; HPLC (Rt): 4.48 min (method O)

The following examples are prepared in analogy to the above described procedure using the corresponding acid (see Acid Intermediates) and amine (see Amine Intermediates) as described before.

| Example | Structure | ESI-MS [M + H]+ | HPLC (Rt) [min] | HPLC method |
| --- | --- | --- | --- | --- |
| 23 | 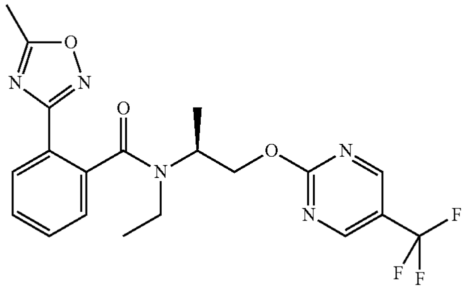 [SMILES: CCN(C(=O)c1ccccc1-c1noc(C)n1)[C@@H](C)COc1ncc(C(F)(F)F)cn1] | 458 [M + Na]+ | 3.41 | N |

Example 25

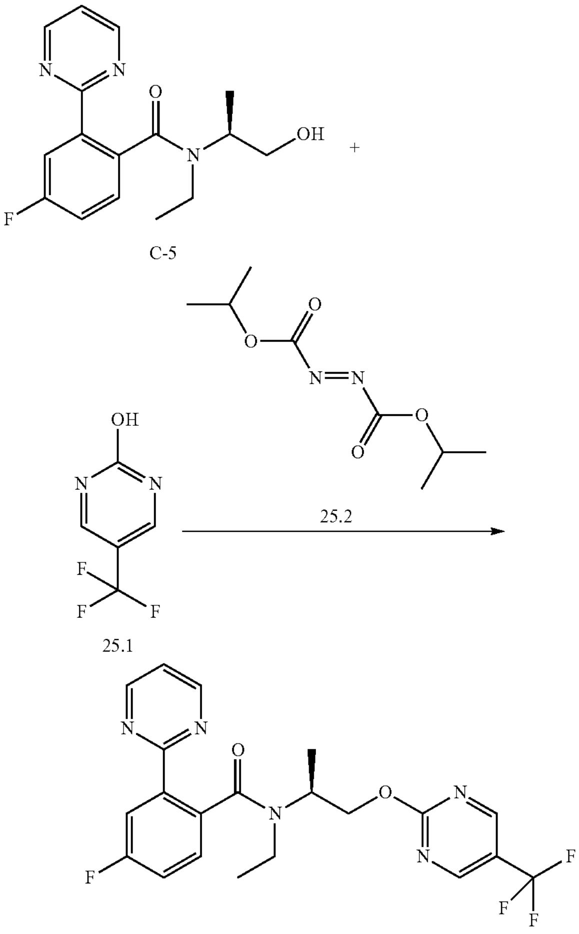

Example 25

To a stirred mixture of polymer bound triphenylphosphine (from Aldrich: catalog number 366455, 3.0 mmol/g, 440 mg, 1.32 mmol) in dry THF (6.0 mL) is added 25.1 (162 mg, 0.99 mmol) and 25.2 (200 mg, 0.99 mmol). After 10 min C-5 (100 mg, 0.33 mmol) is added and the reaction mixture is stirred overnight. The reaction mixture is filtered and the filtrate is concentrated. The crude mixture is taken up in EA and washed with citric acid (10% aq. solution), $Na_2CO_3$ (aq. solution) and water. The mixture is dried and concentrated. The residue is purified by HPLC-MS (using a solvent gradient $H_2O$/ACN with $NH_4COOH$). The obtained product is purified by flash column chromatography on silica gel (using a solvent gradient from 100% cyclohexane to 40% cyclohexane and 60% EA) to provide Example 25 (25 mg). ESI-MS: 472 $[M+H]^+$; HPLC (Rt): 3.45 min (method N)

Example 28

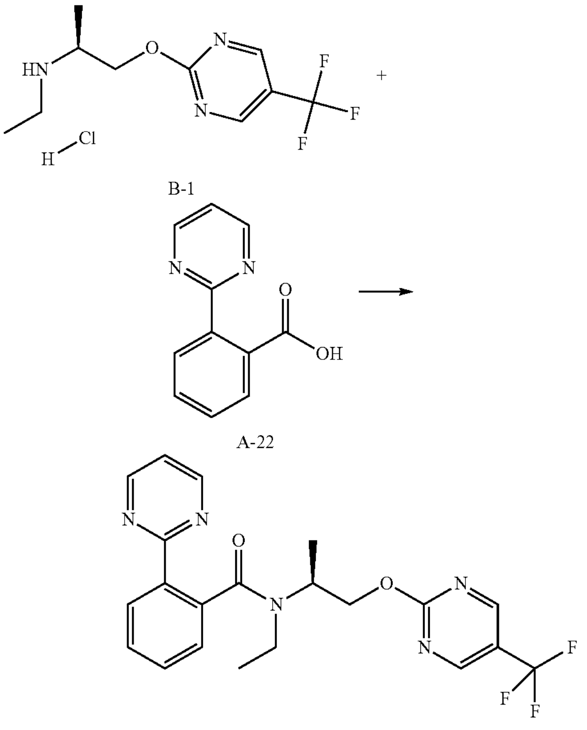

Example 28

To a mixture of A-22 (25 mg, 0.13 mmol), B-1 (30 mg, 0.11 mmol) and DIPEA (54 µl, 0.32 mmol) in dry ACN (2.0 mL) is added CIP (38 mg, 0.14 mmol). The reaction mixture is stirred at 65° C. for 40 min. The reaction mixture is purified by HPLC-MS (using a solvent gradient $H_2O$/ACN with $NH_4OH$) to provide Example 28 (12 mg) ESI pos.+neg. (Loop-Inj.): 432 $[M+H]^+$; HPLC (Rt): 1.03 min (method F)

Example 29

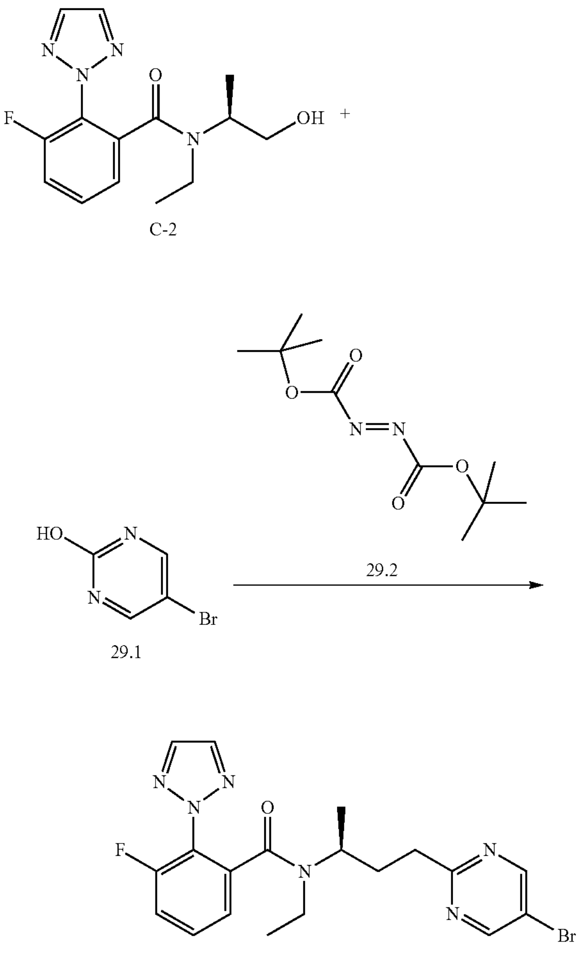
C-2

29.2

29.1

Example 29

To a mixture of C-2 (2.70 g, 9.24 mmol) and 29.1 (1.78 g, 10.2 mmol) in dry THF (30 mL) is added triphenylphosphine (3.15 g, 12.0 mmol) and 29.2 (2.39 g, 230 mmol) and the reaction mixture is stirred at 60° C. for 2 h. The reaction mixture is concentrated, dissolved in DMF and purified by HPLC-MS (using a solvent gradient $H_2O$/ACN with TFA) to provide Example 29 (2.4 g). ESI pos.+neg. (Loop-Inj.): 449 $[M+H]^+$; HPLC (Rt): 1.01 min (method F)

The invention claimed is:

1. A compound of formula I

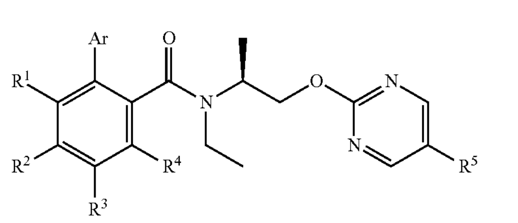
I in which

Ar represents

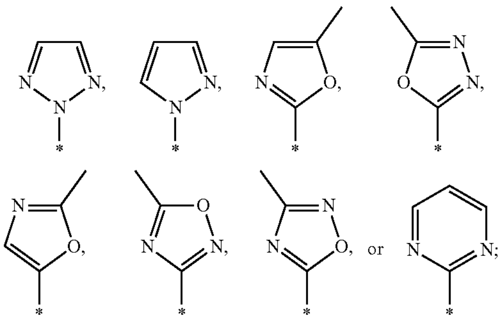
or $R^1$ represents hydrogen, fluoro, or methyl;

$R^2$ and $R^3$ independently represent hydrogen, fluoro, methyl, or $—OCH_3$;

$R^4$ represents hydrogen;

$R^5$ represents bromo or $—CF_3$;

wherein at least two of the substituents $R^1$, $R^2$, $R^3$ and $R^4$ represent hydrogen;

or a pharmaceutically acceptable salt thereof.

2. The compound according to claim 1, wherein $R^2$ represents hydrogen, fluoro, methyl, or $—OCH_3$; and $R^3$ represents hydrogen, fluoro, methyl, or $—OCH_3$.

3. The compound according to claim 1, wherein $R^1$, $R^2$ and $R^3$ independently represent hydrogen or fluoro.

4. The compound according to claim 1, wherein $R^5$ represents $—CF_3$.

5. The compound according to claim 1, wherein

Ar represents

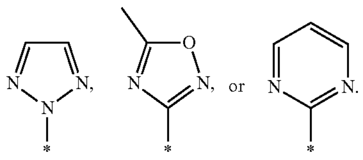
or

6. The compound according to claim 1, wherein

Ar represents

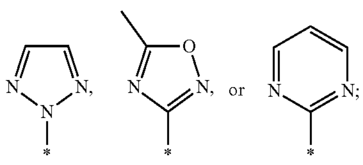
or $R^1$, $R^2$ and $R^3$ independently represent hydrogen or fluoro;

$R^4$ represents hydrogen; and $R^5$ represents $—CF_3$.

7. The compound according to claim 1, selected from the group consisting of
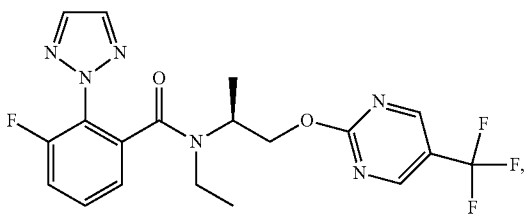
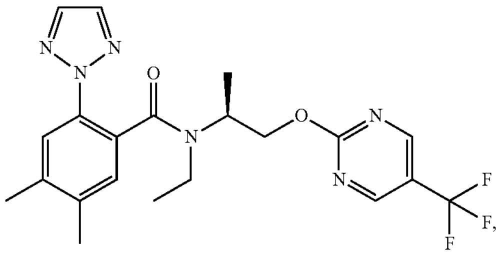
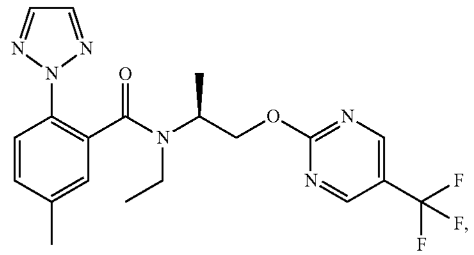
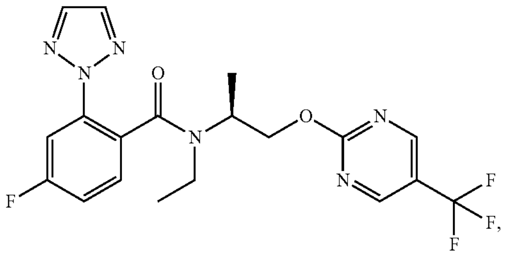
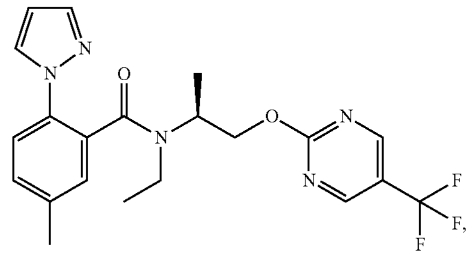
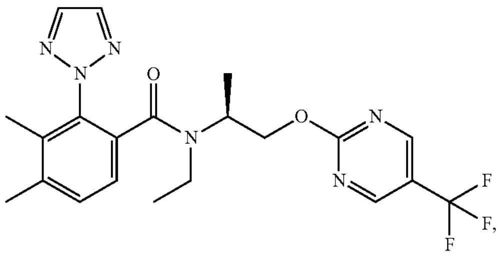
-continued
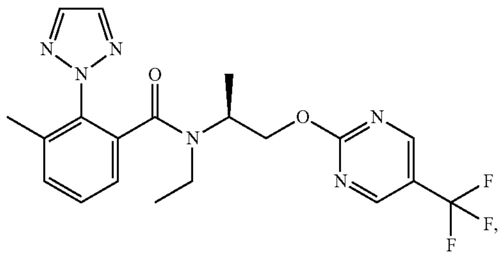
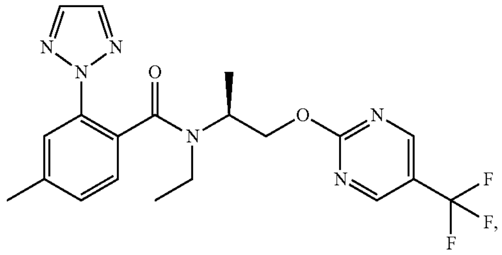
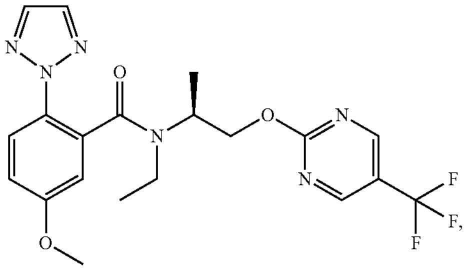
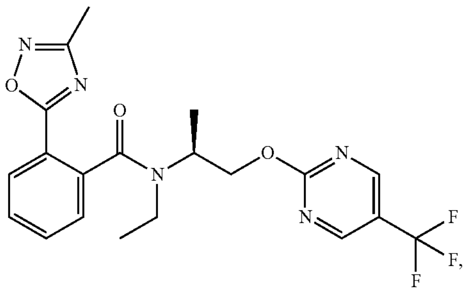
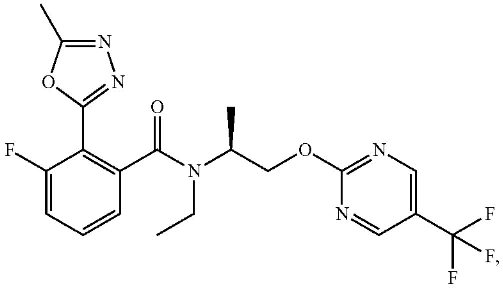
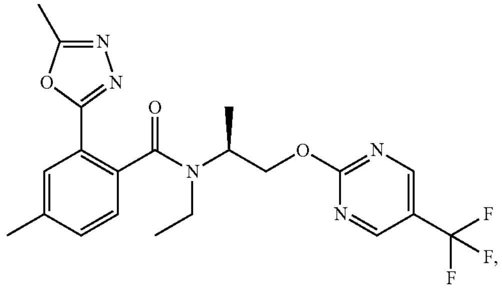

-continued
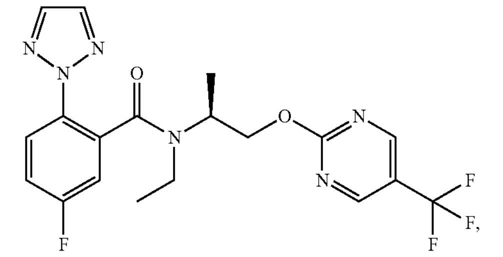
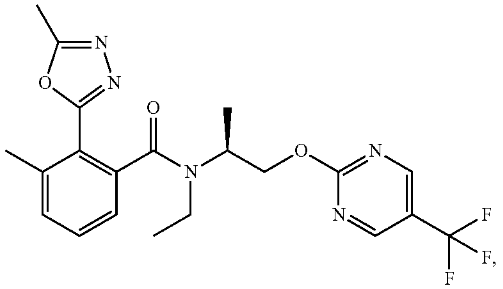
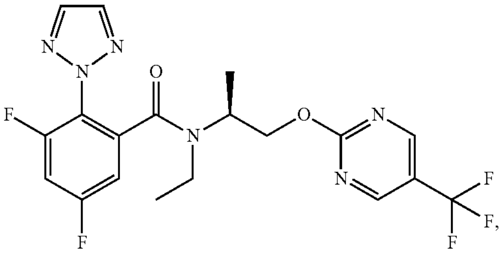
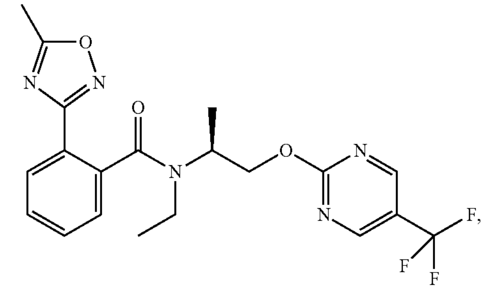
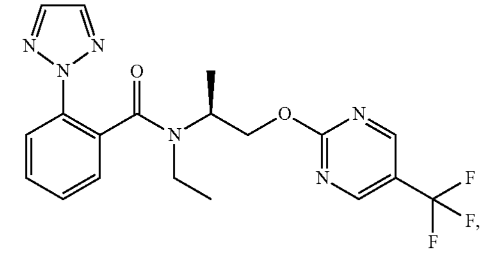
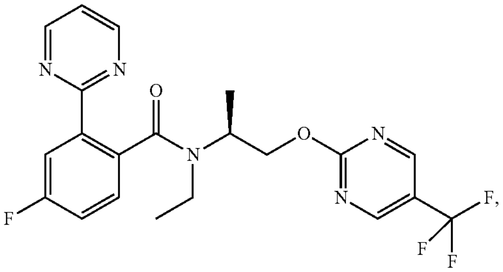
-continued
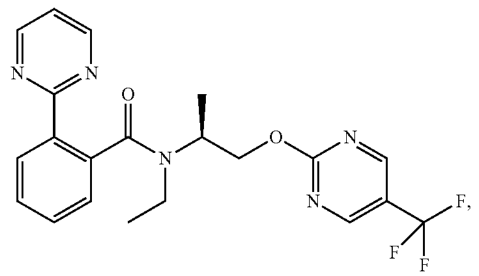
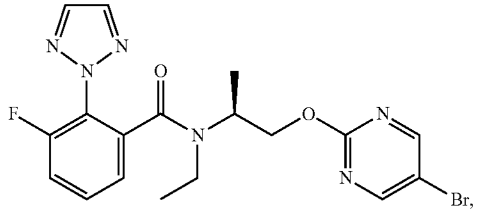
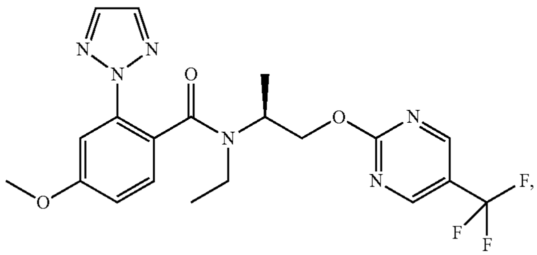
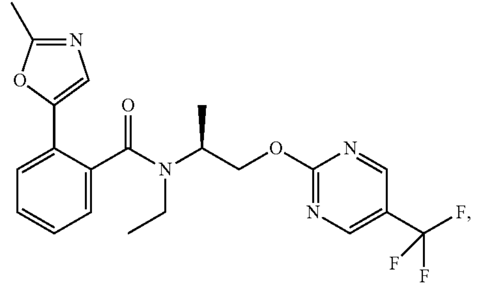
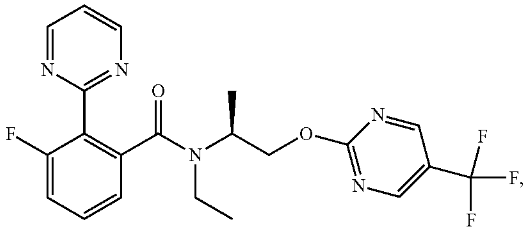
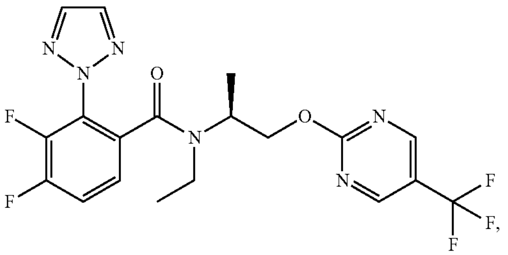
and -continued

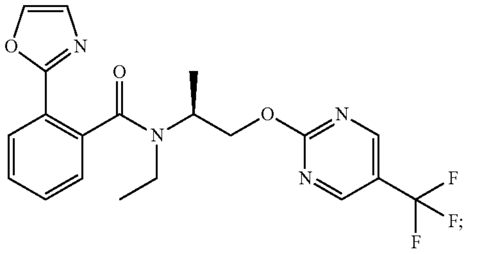 [SMILES: CCN(C(=O)c1ccccc1-c1ncco1)[C@@H](C)COc1ncc(C(F)(F)F)cn1]

or a pharmaceutically acceptable salt thereof.

8. A pharmaceutical composition comprising the compound according to claim 1 or a pharmaceutically acceptable salt thereof in admixture with a pharmaceutically acceptable adjuvant, diluent and/or carrier.

9. A method of treating a psychiatric or neurological condition associated with impulse control deficits, the method comprising administering a compound according to claim 1 or a pharmaceutically acceptable salt thereof, to a patient in need thereof.

10. A pharmaceutically acceptable salt of the compound according to claim 1.

11. The compound according to claim 1 selected from the group consisting of

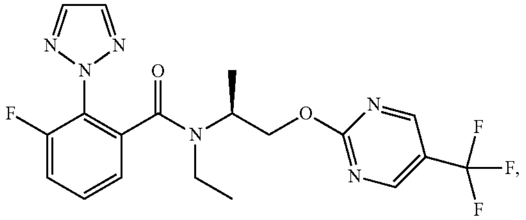

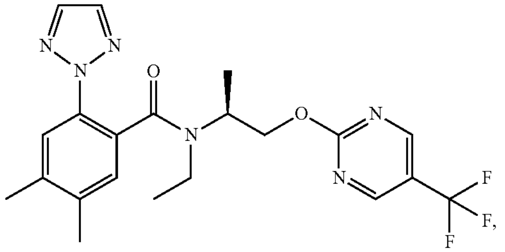

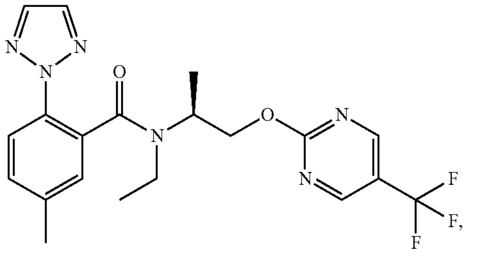

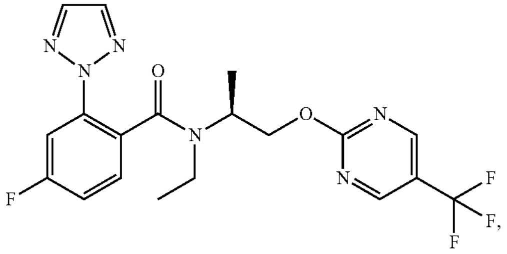

-continued

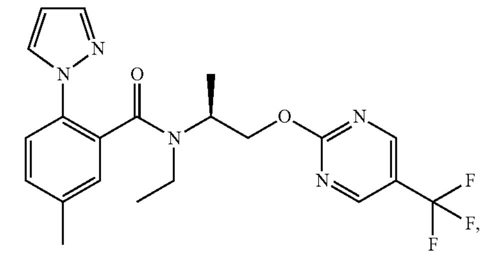

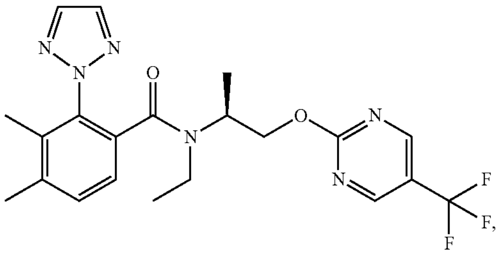

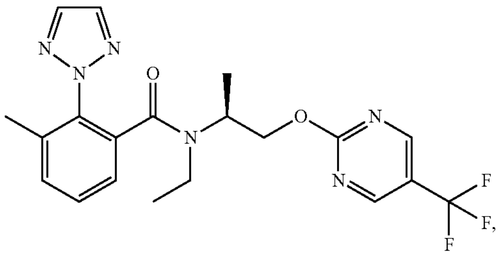

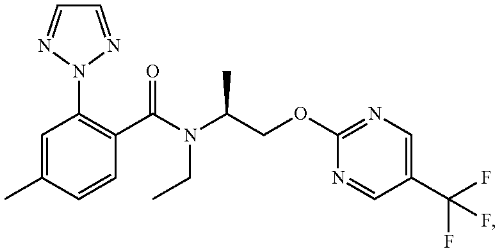

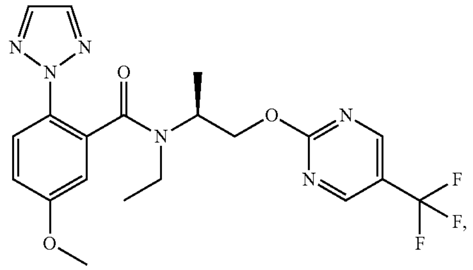

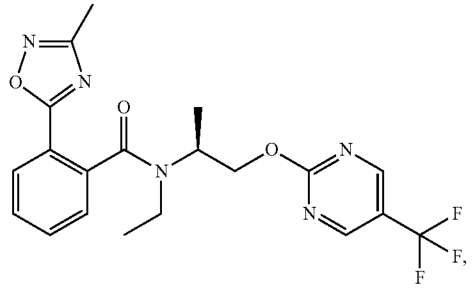

-continued
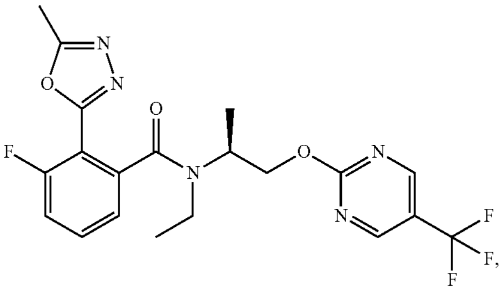
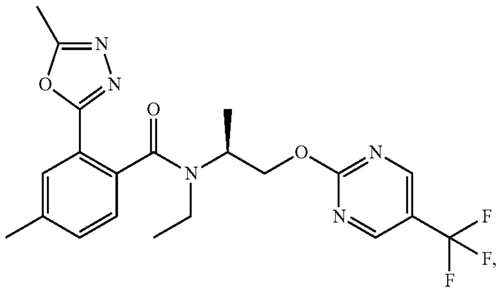
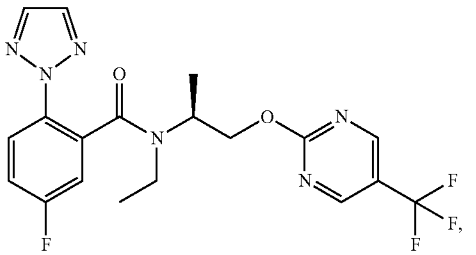
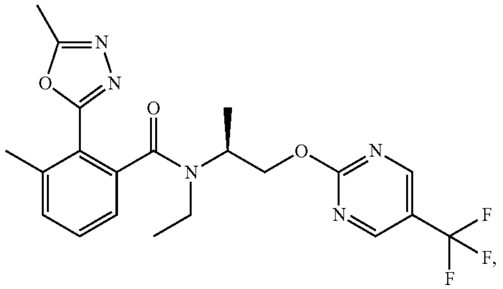
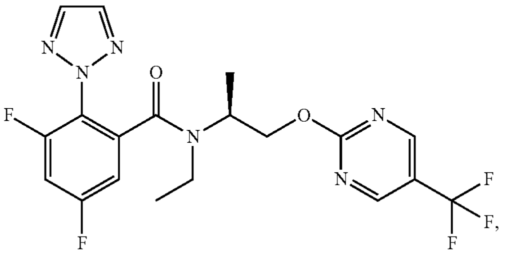
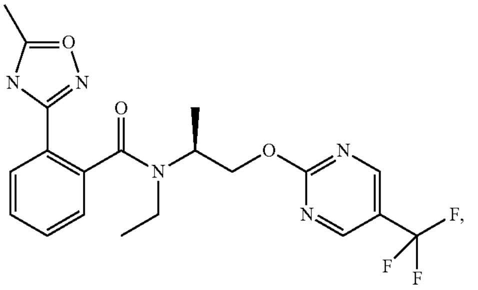
-continued
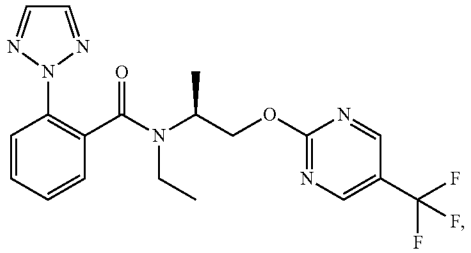
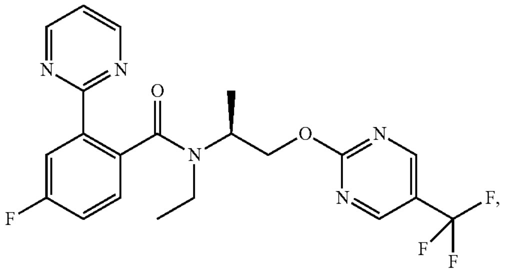
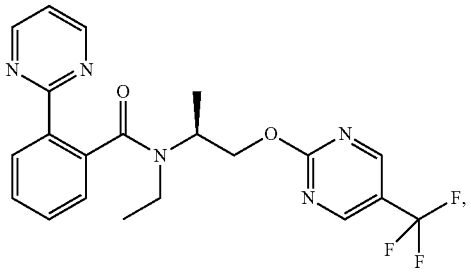
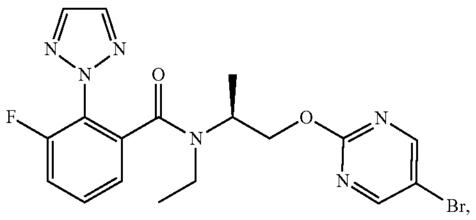
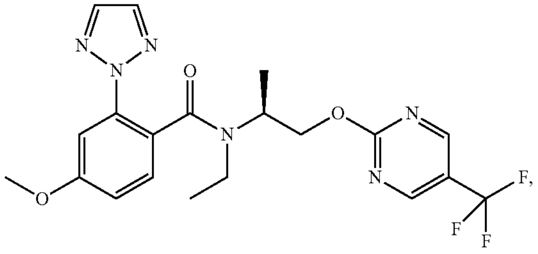
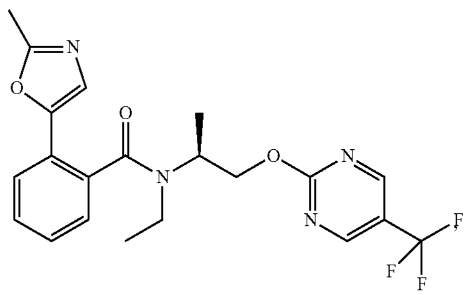

-continued
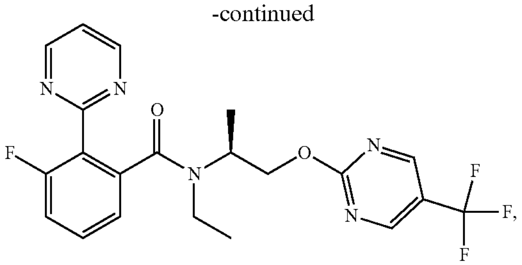
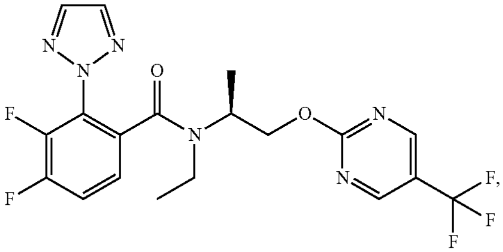 and
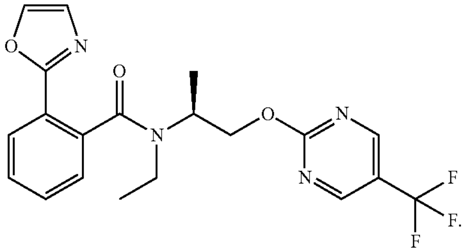 [SMILES: CCN(C(=O)c1ccccc1-c1ncco1)[C@@H](C)COc1ncc(C(F)(F)F)cn1]
* * * * *

UNITED STATES PATENT AND TRADEMARK OFFICE

CERTIFICATE OF CORRECTION

PATENT NO. : 10,392,369 B2
APPLICATION NO. : 16/090325
DATED : August 27, 2019
INVENTOR(S) : Doris Riether et al.

It is certified that error appears in the above-identified patent and that said Letters Patent is hereby corrected as shown below:

On the Title Page

Item (22), PCT filing date:
Change "April 17, 2017" to --April 7, 2017--

Signed and Sealed this
Eighth Day of October, 2019

Andrei Iancu
*Director of the United States Patent and Trademark Office*